(12) United States Patent
Simon et al.

(10) Patent No.: US 9,205,258 B2
(45) Date of Patent: Dec. 8, 2015

(54) NERVE STIMULATOR SYSTEM

(71) Applicant: ElectroCore, LLC, Basking Ridge, NJ (US)

(72) Inventors: Bruce J. Simon, Mountain Lakes, NJ (US); Joseph P. Errico, Warren, NJ (US); Steven Mendez, Chester, NJ (US)

(73) Assignee: Electrocore, LLC, Basking Ridge, NJ (US)

( * ) Notice: Subject to any disclaimer, the term of this patent is extended or adjusted under 35 U.S.C. 154(b) by 2 days.

(21) Appl. No.: 14/071,577

(22) Filed: Nov. 4, 2013

(65) Prior Publication Data

US 2015/0127068 A1 May 7, 2015

(51) Int. Cl.
*A61N 1/00* (2006.01)
*A61N 1/36* (2006.01)

(52) U.S. Cl.
CPC .......... *A61N 1/3605* (2013.01); *A61N 1/36153* (2013.01); *A61N 1/36175* (2013.01)

(58) Field of Classification Search
CPC ........... A61N 1/37223; A61N 1/37205; A61N 1/37211; A61N 1/372
USPC .......................................................... 607/60
See application file for complete search history.

(56) References Cited

U.S. PATENT DOCUMENTS

| 3,590,810 | A | 7/1971 | Kopecky |
| 4,196,737 | A | 4/1980 | Bevilacqua |
| 5,458,141 | A | 10/1995 | Neil |
| 5,733,313 | A * | 3/1998 | Barreras et al. ............. 607/33 |
| 5,899,922 | A | 5/1999 | Loos |
| 5,983,131 | A | 11/1999 | Weaver et al. |
| 6,341,236 | B1 | 1/2002 | Osorio et al. |
| 6,463,327 | B1 | 10/2002 | Lurie et al. |
| 6,587,719 | B1 | 7/2003 | Barrett et al. |
| 6,610,713 | B2 | 8/2003 | Tracey |
| 7,797,041 | B2 | 9/2010 | Libbus et al. |
| 2002/0099417 | A1 | 7/2002 | Naritoku et al. |

(Continued)

FOREIGN PATENT DOCUMENTS

| WO | WO 93/01862 | 2/1993 |
| WO | WO 2009/021080 | 2/2009 |
| WO | WO 2009/135693 | 11/2009 |

OTHER PUBLICATIONS

Greicius et al., Functional connectivity in the resting brain: A network analysis of the default mode hypothesis, PNAS, Jan. 2003, vol. 100, No. 1, pp. 253-258.

(Continued)

*Primary Examiner* — Robert N Wieland
(74) *Attorney, Agent, or Firm* — Dentons US LLP

(57) ABSTRACT

Devices, systems and methods for applying electrical impulse(s) to one or more selected nerves are described. An electrical stimulator is introduced through a to a target location within, adjacent to, or in close proximity with, the carotid sheath. The stimulator has an antenna that allows it to be powered solely by far-field or approximately plane wave electromagnetic radiation, having frequencies in the range of 0.3 to 10 GHz. Electrical impulses are applied through the stimulator to a vagus nerve to stimulate, block or otherwise modulate activity of the nerve and treat the patient's condition. The stimulator uses an adjustable number of fixed voltage (or fixed current) pulses with fixed duration to elicit desired changes in nerve response, the timing of which are controlled by an external power transmitter and controller.

35 Claims, 13 Drawing Sheets

(56) References Cited

U.S. PATENT DOCUMENTS

| | | | |
|---|---|---|---|
| 2002/0183237 A1 | 12/2002 | Puskas | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0137644 A1 | 6/2005 | Boveja et al. | |
| 2006/0074284 A1 | 4/2006 | Juola et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0132964 A1 | 6/2008 | Cohen et al. | |
| 2008/0177190 A1 | 7/2008 | Libbus et al. | |
| 2008/0208266 A1 | 8/2008 | Lesser et al. | |
| 2008/0306325 A1 | 12/2008 | Burnett et al. | |
| 2009/0048643 A1* | 2/2009 | Erickson et al. | 607/59 |
| 2009/0157149 A1 | 6/2009 | Wahlgren et al. | |
| 2009/0234419 A1 | 9/2009 | Maschino et al. | |
| 2009/0287035 A1 | 11/2009 | Dietrich et al. | |
| 2010/0280575 A1* | 11/2010 | Carbunaru et al. | 607/59 |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029601 A1 | 2/2012 | Simon et al. | |
| 2012/0215278 A1* | 8/2012 | Penner | 607/42 |
| 2012/0283697 A1 | 11/2012 | Kim et al. | |
| 2012/0303080 A1 | 11/2012 | Ben-David et al. | |
| 2012/0310306 A1* | 12/2012 | Klostermann et al. | 607/60 |
| 2013/0138173 A1* | 5/2013 | Bianchi et al. | 607/25 |
| 2013/0245722 A1* | 9/2013 | Ternes et al. | 607/62 |
| 2013/0289650 A1* | 10/2013 | Karlsson et al. | 607/44 |
| 2014/0081354 A1* | 3/2014 | Davis et al. | 607/59 |
| 2014/0249594 A1* | 9/2014 | Sharma et al. | 607/40 |
| 2014/0336727 A1* | 11/2014 | Perryman et al. | 607/59 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

* cited by examiner

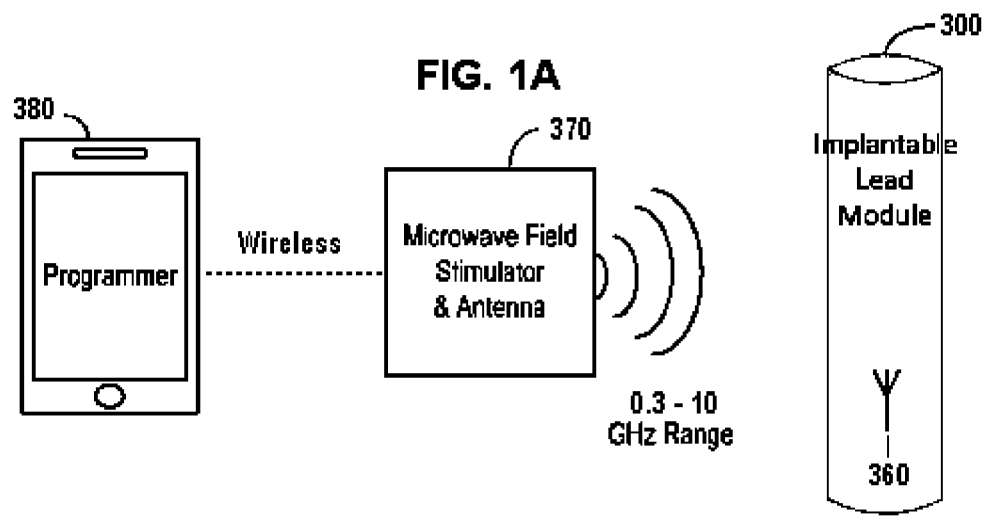
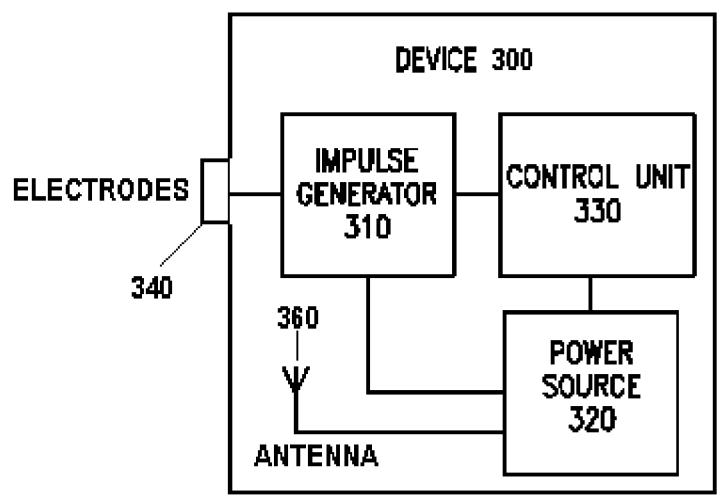

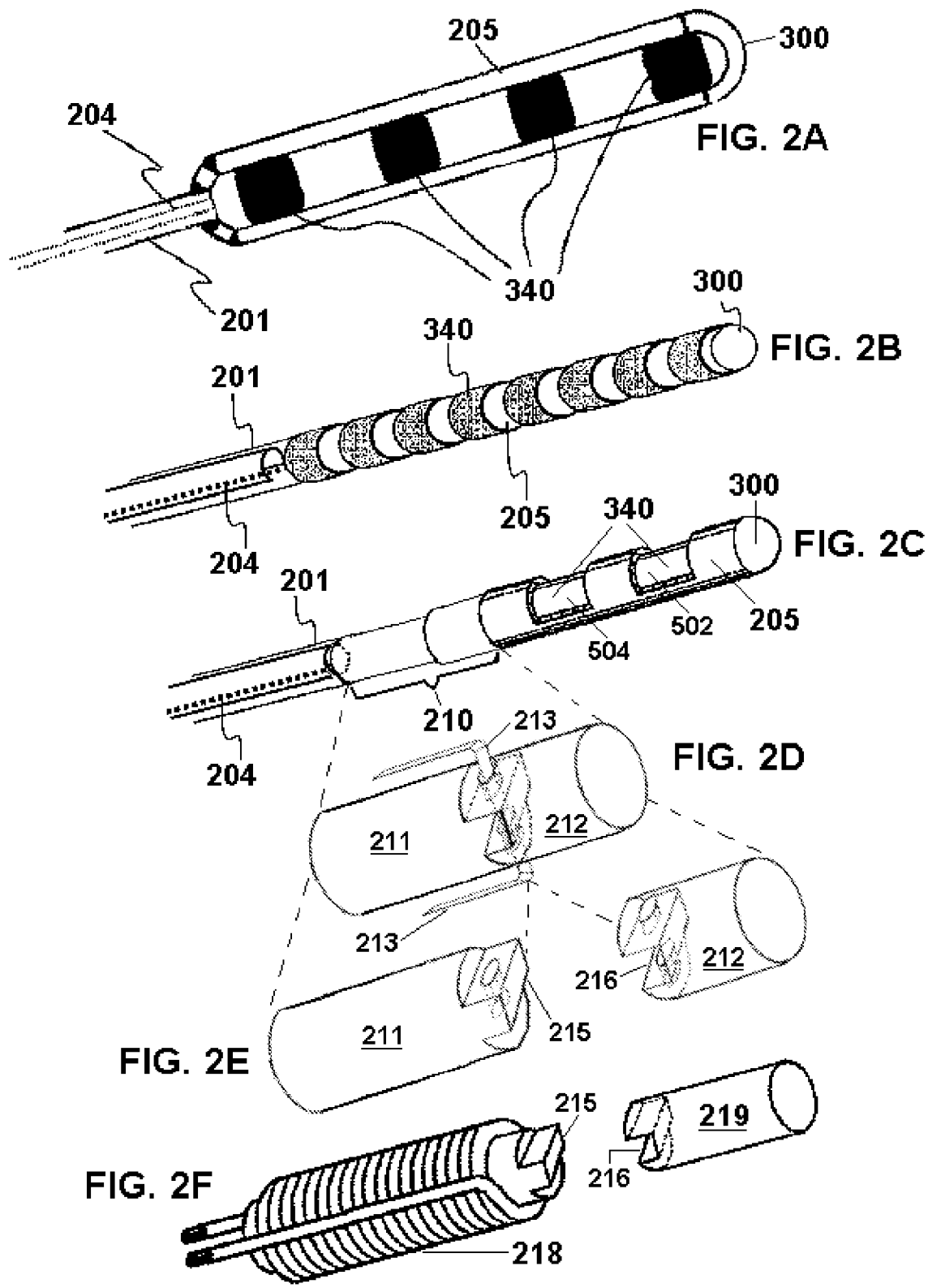

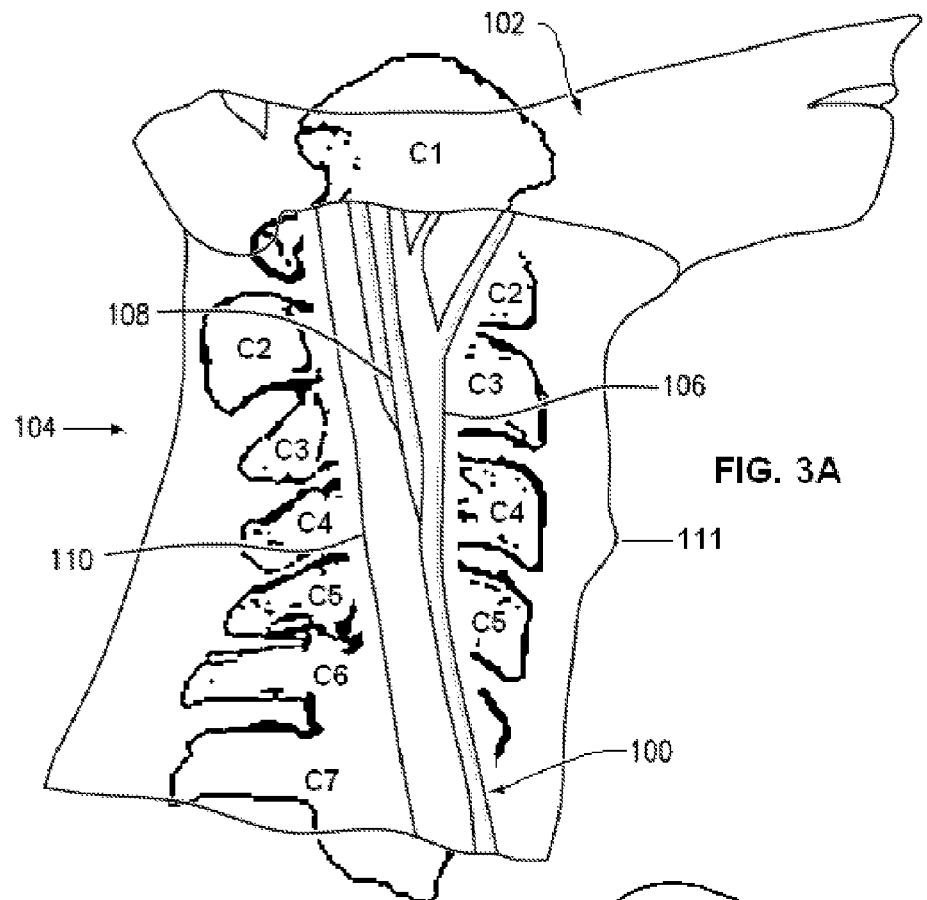
FIG. 3A
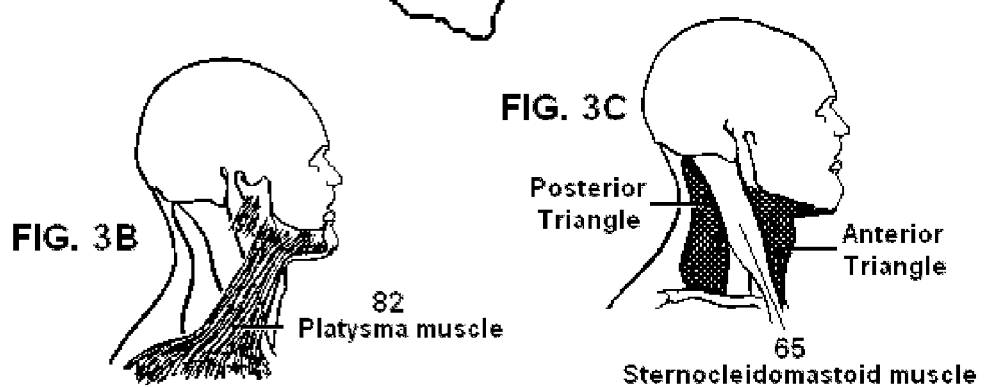
FIG. 3B
FIG. 3C

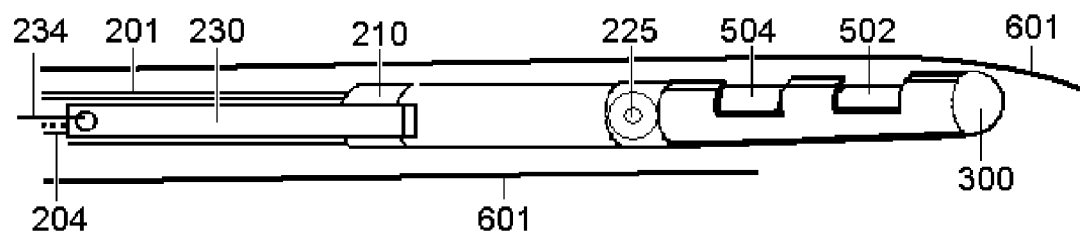
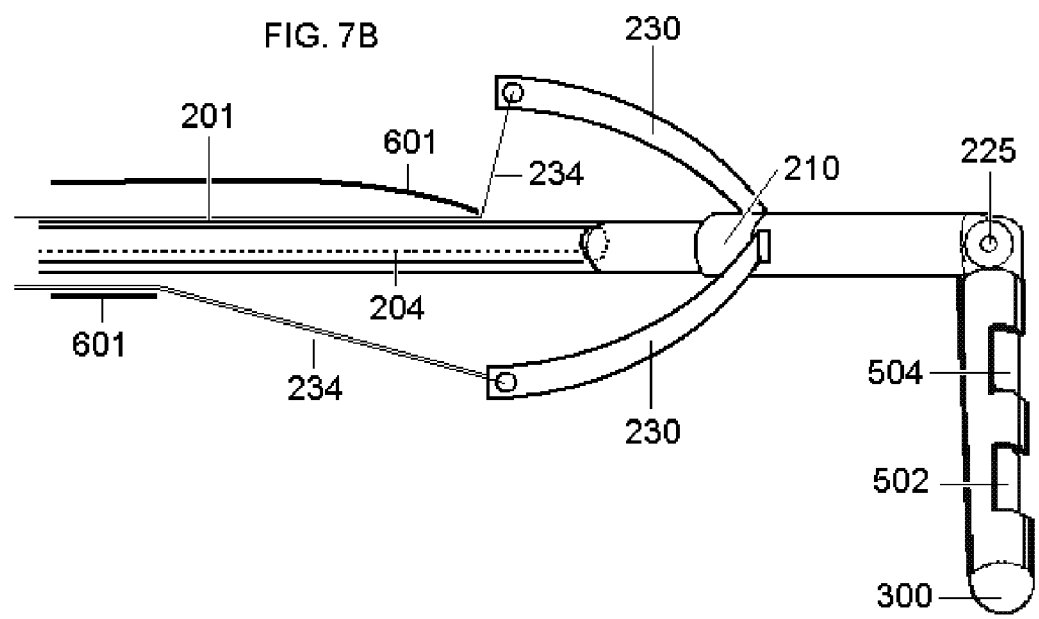

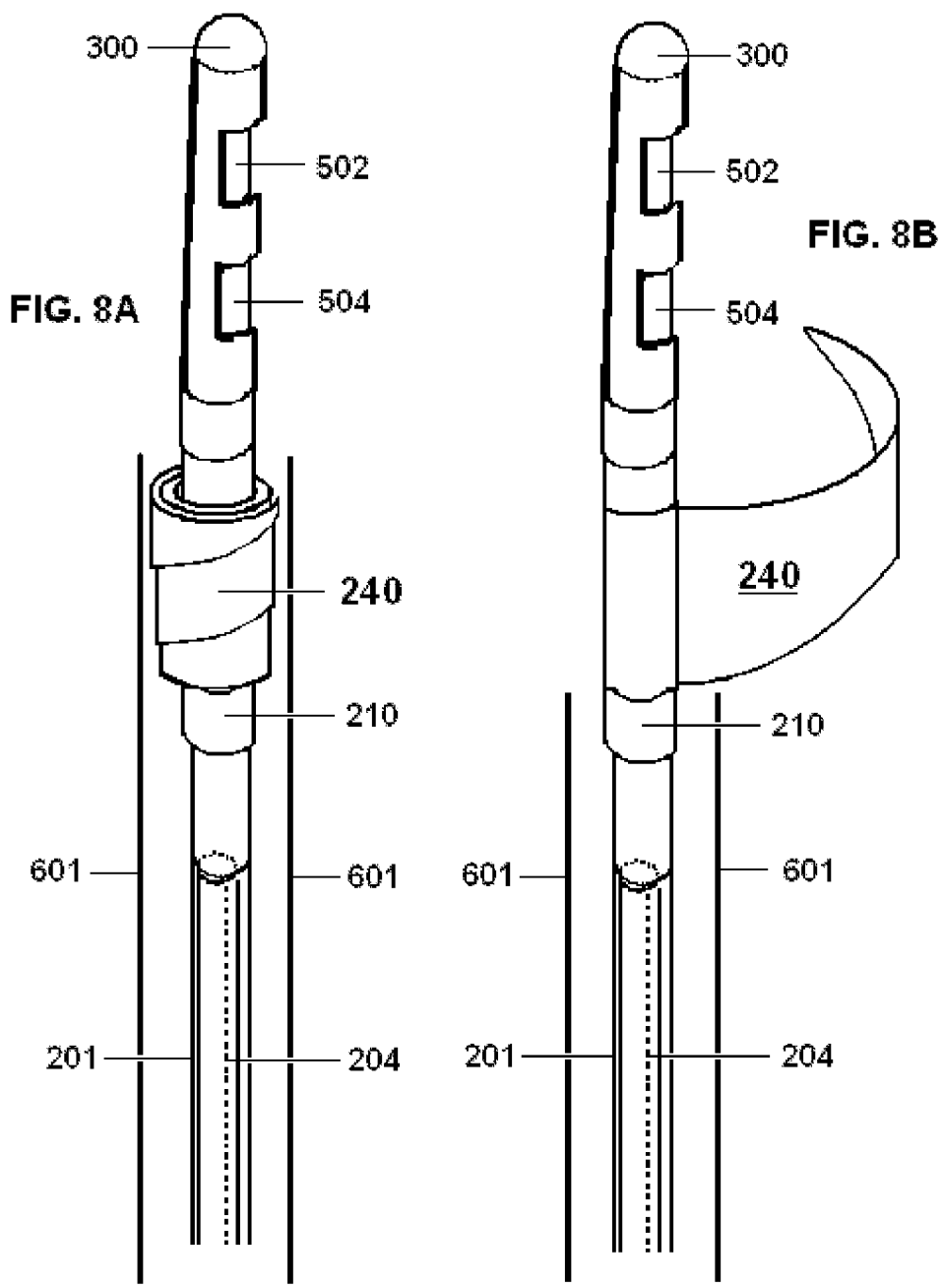

NERVE STIMULATOR SYSTEM

FIELD

The field of the present invention relates to the delivery of energy impulses (and/or fields) to bodily tissues for therapeutic purposes. The energy impulses (and/or fields) that are used to treat those conditions comprise electrical and/or electromagnetic energy, which are delivered to nerve or other tissue of a patient.

BACKGROUND OF THE INVENTION

The use of electrical stimulation for treatment of medical conditions is well known. One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667, entitled Implantable medical device for treating cardiac mechanical dysfunction by electrical stimulation, to DENO et al). Because the leads are implanted within the patient, the pacemaker is an example of an implantable medical device.

Another such example is electrical stimulation of the brain with implanted electrodes (deep brain stimulation), which has been approved for use in the treatment of various conditions, including pain and movement disorders such as essential tremor and Parkinson's disease [Joel S. PERLMUTTER and Jonathan W. Mink. Deep brain stimulation. Annu. Rev. Neurosci 29 (2006):229-257].

Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92(2001):505-513; patent U.S. Pat. No. 6,871,099, entitled Fully implantable microstimulator for spinal cord stimulation as a therapy for chronic pain, to WHITEHURST et al].

Many other forms of nerve stimulation exist [HATZIS A, Stranjalis G, Megapanos C, Sdrolias P G, Panourias I G, Sakas D E. The current range of neuromodulatory devices and related technologies. Acta Neurochir Suppl 97(Pt 1, 2007): 21-29]. The type of electrical stimulation that is most relevant to the present invention is vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first implanting an electrode about the vagus nerve during open neck surgery and by then connecting the electrode to an electrical stimulator circuit (a pulse generator). The pulse generator is ordinarily implanted subcutaneously within a subcutaneous pocket that is created at some distance from the electrode, which is usually in the left infraclavicular region of the chest, but it may also be implanted in a deeper pocket beneath the pectoralis major muscle. A lead is then tunneled subcutaneously to connect the electrode assembly and pulse generator. The patient's stimulation protocol is then programmed using a device (a programmer) that communicates with the pulse generator, with the objective of selecting stimulation parameters that best treat the patient's condition (pulse frequency, stimulation amplitude, pulse width, etc.) [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009):1042-1060; GROVES D A, Brown V J. Vagal nerve stimulation: a review of its applications and potential mechanisms that mediate its clinical effects. Neurosci Biobehav Rev 29(2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (March, 2008):E9, pp. 1-4; ANDREWS, R. J. Neuromodulation. I. Techniques-deep brain stimulation, vagus nerve stimulation, and transcranial magnetic stimulation. Ann. N. Y. Acad. Sci. 993(2003):1-13; LABINER, D. M., Ahern, G. L. Vagus nerve stimulation therapy in depression and epilepsy: therapeutic parameter settings. Acta. Neurol. Scand. 115(2007):23-33; AMAR, A. P., Levy, M. L., Liu, C. Y., Apuzzo, M. L. J. Vagus nerve stimulation. Proceedings of the IEEE 96(July, 2008):1142-1151; BEEKWILDER J P, Beems T. Overview of the clinical applications of vagus nerve stimulation. J Clin Neurophysiol 27(February, 2010):130-138; CLANCY J A, Deuchars S A, Deuchars J. The wonders of the Wanderer. Exp Physiol 98(January, 2013):38-45].

For vagus nerve stimulators that are currently implanted in patients, the pulse generator contains a battery that powers the system. With typical stimulator settings, the battery life range may be as long as 6.6 to 10 years, but maybe as short as less than two years. Eventually the battery must be surgically replaced when it is at or near the limit of its lifetime [Depression Patient's Manual for Vagus Nerve Stimulation with the VNS Therapy System. Document REF 26-0005-6000/1, 2004. Cyberonics Inc. 100 Cyberonics Boulevard, Houston, Tex. U.S.A. 77058; VONCK K, Dedeurwaerdere S, De Groote L, Thadani V, Claeys P, Gossiaux F, Van Roost D, Boon P. Generator replacement in epilepsy patients treated with vagus nerve stimulation. Seizure 14(February, 2005): 89-99].

However, beginning with some of the earliest implantable systems, nerve stimulators have been developed that contain no battery whatsoever, or that use a rechargeable battery that is charged by an energy source situated outside the body of the patient. Already in 1934, CHAFFEE and LIGHT successfully stimulated the thoracic vagus nerve of an animal with an implanted electrode powered only by an externally applied electromagnetic field, as evidenced by the production of gastric acid from the animal [E. Leon CHAFFEE and Richard U. Light. A Method for the Remote Control of Electrical Stimulation of the Nervous System. Yale J Biol Med 7(February, 1934): 83-128]. Smaller implanted peripheral nerve and brain stimulators that had no battery were subsequently developed for use in patients in the 1960s [William W. L. GLENN, John H. Hageman, Alexander Mauro, Lawrence Eisenberg, Stevenson Flanigan, and Marvin Harvard. Electrical Stimulation of Excitable Tissue by Radio-Frequency Transmission. Ann Surg 160(March, 1964):338-350; DELGADO J M. Radiostimulation of the brain in primates and man. Anesth Analg 48(April, 1969):529-542]. Such systems transfer energy inductively to the implanted stimulator, from a coil outside the patient's body to an implanted coil, such that the implanted coil supplies power to the stimulator's electrodes or to an implanted rechargeable battery [U.S. Pat. No. 3,727,616, entitled Electronic system for the stimulation of biological systems, to LENKES; U.S. Pat. No. 7,813,809, entitled Implantable pulse generator for providing functional and/or therapeutic stimulation of muscles and/or nerves and/or central nervous system tissue, to STROTHER et al; U.S. Pat. No. 8,369,959, entitled Implantable medical device with integrated antenna system, to MESKENS; U.S. Pat. No. 6,782,292, entitled System and method for treatment of mood and/or anxiety disorders by electrical brain stimulation and/or drug infusion, to WHITEHURST; application US20030212440, entitled Method and system for modulating the vagus nerve (10th cranial nerve) using modulated electrical pulses with an inductively coupled stimulation system, to BOVEJA].

Such inductive systems may also be used for bidirectional telemetry of device parameter settings and physiological data, irrespective of whether the devices are also powered by induction coils [Robert PUERS and Jef Thoné. Short distance wireless communications. Chapter 7, pp. 219-277, In: H.-J. Yoo, C. van Hoof (eds.), Bio-Medical CMOS ICs. New York: Springer, 2011; U.S. Pat. No. 5,186,170, entitled Simultaneous radio frequency and magnetic field microprocessor reset circuit, to VARRICHIO et al]. Intrinsic limitations of such coil-based powering systems are that the source oscillating magnetic field must be in close proximity to the implanted pickup coil in order to transfer the energy efficiently (e.g., applied to the patient's skin), and the source and pickup coils have to be optimally oriented with respect to one another. The frequencies of oscillations for those systems involving magnetic induction are typically less than 100 MHz.

The stimulators could also be powered by ultrasound or infrared light, in which case the energy source would also likely have the disadvantage of having to be placed close to the implant [ABDO A, Sahin M, Freedman D S, Cevik E, Spuhler P S, Unlu M S. Floating light-activated microelectrical stimulators tested in the rat spinal cord. J Neural Eng 8(May, 2011):056012, pp. 1-9; GULICK D W, Towe B C. Method of locating ultrasound-powered nerve stimulators. Conf Proc IEEE Eng Med Biol Soc. 2012; 2012:887-890].

However, this proximity problem would not occur if the device were powered by electrochemical energy supplied by the tissue of the patient [MERCIER P P, Lysaght A C, Bandyopadhyay S, Chandrakasan A P, Stankovic K M. Energy extraction from the biologic battery in the inner ear. Nat Biotechnol 30(December, 2012):1240-1243]. Energy scavenging from other sources, such as body movement, may in principle also be used for autonomous, batteryless powering [E. M. YEATMAN. Advances In Power Sources For Wireless Sensor Nodes. Proceedings of 1st International Workshop on Body Sensor Networks, London, Apr. 6-7, 2004, pp. 20-21; Joseph A. PARADISO and Thad Starner. Energy Scavenging for Mobile and Wireless Electronics. IEEE Pervasive Computing 4(January, 2005):18-27].

Another potential source of scavenged energy is ambient radio waves, e.g., as used in crystal radio sets. However, that potential source is generally limited to situations in which very little power is needed for the device, or the environment contains an unusually high level of ambient electromagnetic energy [E. M. YEATMAN. Advances In Power Sources For Wireless Sensor Nodes. Proceedings of 1st International Workshop on Body Sensor Networks, London, Apr. 6-7, 2004, pp. 20-21; Joseph A. PARADISO and Thad Starner. Energy Scavenging for Mobile and Wireless Electronics. IEEE Pervasive Computing 4(January, 2005):18-27; Rick ROBINSON. Air Power: New Device Captures Ambient Electromagnetic Energy to Drive Small Electronic Devices. Georgia Tech Research News. Research News & Publications Office. Georgia Institute of Technology, 75 Fifth Street, N.W., Suite 314, Atlanta, Ga. 30308, 2011, pp. 1-3; Vikram GUPTA, Arvind Kandhalu, Ragunathan (Raj) Rajkumar. Energy Harvesting from Electromagnetic Energy Radiating from AC Power Lines. Proceedings of the 6th Workshop on Hot Topics in Embedded Networked Sensors. Killarney, Ireland, June 2010. Article No. 17, pp. 1-5; Soheil RADIOM, Majid Baghaei-Nejad, Guy Vandenbosch, Li-Rong Zheng, Georges Gielen. Far-field RF Powering System for RFID and Implantable Devices with Monolithically Integrated On-Chip Antenna. In: Proc. Radio Frequency Integrated Circuits Symposium (RFIC), 2010 IEEE, Anaheim, Calif., 23-25 May 2010, pp. 113-116; J. H. HWANG, C. H. Hyoung, K. H. Park and Y. T. Kim. Energy harvesting from ambient electromagnetic wave using human body as antenna. Electronics Letters 49(February, 2013):149-151; MANTIPLY E D, Pohl K R, Poppell S W, Murphy J A. Summary of measured radiofrequency electric and magnetic fields (10 kHz to 30 GHz) in the general and work environment. Bioelectromagnetics 18(August, 1997):563-577; FLODERUS B, Stenlund C, Carlgren F. Occupational exposures to high frequency electromagnetic fields in the intermediate range (>300 Hz-10 MHz). Bioelectromagnetics 23(August, 2002):568-577].

The proximity problem would also not arise if higher-frequency beamed electromagnetic waves were used to supply power as now described. Recently, systems have been developed that power implanted pulse generators (or their rechargeable battery) using electromagnetic fields with frequencies on the order of 300 MHz to 10 GHz. An advantage of using these frequencies is that it does not ordinarily require the source of the fields be in the immediate proximity of the receiving antenna within the implanted device. For example, a horn antenna with a waveguide may be used to direct the radiation from its source to a receiving implant antenna that is several meters away from the horn. Some of these devices may operate either in the inductive mode that was described in a previous paragraph, or in the higher frequency mode wherein the electromagnetic field supplying the stimulator's power is propagated as a far-field or approximate plane wave [application US20120004708, entitled Implantable medical device and charging system employing electric fields, to CHEN et al]. Other such devices are designed to operate only at the higher frequencies. They may receive power using a rectenna, or more generally using a dipole, slot, patch, or other type of antenna that can be used to receive power at these frequencies [application US20130018438, entitled Far field radiative powering of implantable medical therapy devices, to CHOW; US20130018439, entitled Implantable nerve wrap for nerve stimulation configured for far field radiative powering, to CHOW; US20130018440, entitled Powering of an implantable medical therapy delivery device using far field radiative powering at multiple frequencies, to CHOW].

PERRYMAN et al also disclosed implantable neural stimulators that are powered by electromagnetic radiation at the higher frequencies, comprising one or more electrodes, a dipole antenna, and stimulation circuitry, but no internally-supplied power source. Power to the stimulator is supplied through the stimulator's dipole antenna, which is configured to receive electrical energy from a second external antenna, using electrical radiative coupling (i.e., coupling to far field or approximately plane wave radiation). That energy is then used to electrically stimulate bodily tissue adjacent to the device's electrodes, such as a peripheral nerve. The device is also configured to generate a feedback signal, which is sent from the stimulator's dipole antenna back to the second antenna, also through electrical radiative coupling. In some embodiments, an intermediate "relay module" is configured to generate the actual radiofrequency wave that is received by the implanted neural stimulator, for example, with the relay module placed under the skin over the vagus nerve in the neck [WO/2012/138782, entitled Implantable lead, to PERRYMAN et al. US20120283800, entitled Neural Stimulator System, to PERRYMAN et al. US20120330384, entitled Remote control of power or polarity selection for a neural stimulator, to PERRYMAN et al. US20130066400, entitled Microwave field stimulator, to PERRYMAN et al. US20130079849, entitled Relay module for implant, to PERRYMAN et al].

It is understood that implanted devices operating with the higher frequency electromagnetic radiation may also be used for bidirectional telemetry of device parameters or of physiological data, irrespective of whether operational power is also supplied by a transmitter operating within those frequencies. For example, telemetry may take place in the Medical Implant Communication Service band (MICS) of 402-405 MHz, and early implanted telemetry systems with a battery operated with frequencies of 100 to 500 MHz with a range of about 30 meters [DELGADO J M, Mark V, Sweet W, Ervin F, Weiss G, Bach-Y-Rita G, Hagiwara R. Intracerebral radio stimulation and recording in completely free patients. J Nery Ment Dis 147(April, 1968):329-340; Eric Y CHOW. Wireless miniature implantable devices and asics for monitoring, treatment, and study of glaucoma and cardiac disease. PhD Dissertation, West Lafayette, Ind.: Purdue University, 2009; Robert PUERS and Jef Thoné. Short distance wireless communications. Chapter 7, pp. 219-277. In: H.-J. Yoo, C. van Hoof (eds.), Bio-Medical CMOS ICs. New York: Springer, 2011].

In addition to the need to replace a battery, another disadvantage of conventional implanted vagus or peripheral nerve stimulation systems is the mechanical stress and the resulting chronic tissue response caused by the constant movement of tethering electrical cables that are connected to the pulse generator. Furthermore, the cables may break, and motion of the cables may cause their attached electrode assemblies to migrate or rotate, causing the stimulation system to fail. These problems are not unique to vagus nerve stimulators, but occur also with systems that stimulate other peripheral nerves and the spine [Konstantin V. SLAVIN. Technical Aspects of Peripheral Nerve Stimulation: Hardware and Complications. pp. 189-202 In: Konstantin V. SLAVIN (ed). Peripheral Nerve Stimulation. Progress in Neurological Surgery Vol. 24. Basel (Switzerland): Karger A G, 2011; KIM D D, Vakharyia R, Kroll H R, Shuster A. Rates of lead migration and stimulation loss in spinal cord stimulation: a retrospective comparison of laminotomy versus percutaneous implantation. Pain Physician 14(June, 2011):513-524]. The same may be true for the above cited-patent applications that are powered at the higher electromagnetic frequencies. The application by CHEN uses conventional cables and pulse generators, except that they may be powered by electromagnetic radiation at the higher frequencies. An above-cited application by PERRYMAN et al does not contain a separate pulse generator and tethering cables connected to the electrode assembly, but it does have a tethered "extension tubing," with a lumen that is used with a stylet to facilitate implantation of the stimulator. In one embodiment of their invention, the system's antenna extends into the tubing [WO/2012/138782, entitled Implantable lead, to PERRYMAN et al]. After the electrodes are implanted, the tubing is shown to be left in place, and its end is anchored under the skin near the site of implant entry. Thus, the system described by PERRYMAN et al. would also cause tissue response problems, owing to the movement of the tethering tubing, for the same reason that a tethering electrical cable causes problems.

Nevertheless, there do exist implanted externally-powered nerve stimulation systems that do not contain a tethered lead or tubing after implantation. Unfortunately, however, those systems are powered externally by inductive coils, not by the higher frequency approximately plane wave or far-field electromagnetic radiation. They therefore suffer from the disadvantage that an external coil providing energy to the implanted stimulator must be very close to the implanted pickup coil in order to transfer energy efficiently. Two such systems are BION devices and microtransponder devices.

The simplest version of BION stimulators consist of wireless micromodules, each of which receives power and command signals by inductive coupling from an external antenna. Its electronic components are housed in a hermetically sealed glass capsule, which is 2 mm in diameter×16 mm in length, which is small enough to be implanted through a 12 gauge hypodermic needle. Each device delivers monophasic stimulation pulses through a tantalum capacitor electrode. The later BION versions contain a rechargeable battery that allows sufficient power for external programming and advanced telemetry. In that regard, the later BION stimulators resemble miniature stimulators that were described by WHITEHURST et al [LOEB G E, Zamin C J, Schulman J H, Troyk P R. Injectable microstimulator for functional electrical stimulation. Med Biol Eng Comput 29(June, 1991):NS13-NS19; CAMERON T, Loeb G E, Peck R A, et al: Micromodular implants to provide electrical stimulation of paralyzed muscles and limbs. IEEE Trans Biomed Eng 44(September, 1997):781-790; LOEB G E, Richmond F J, Baker L L. The BION devices: injectable interfaces with peripheral nerves and muscles. Neurosurg Focus 20(May, 2006):E2, pp. 1-9; Todd K. WHITEHURST, Joseph H. Schulman, Kristen N. Jaax, and Rafael Carbunaru. The BionMicrostimulator and its Clinical Applications. pp. 253-273. In: D. D. Zhou, E. Greenbaum (eds.). Implantable Neural Prostheses 1. Devices and Applications. New York, N.Y.: Springer-Verlag, 2009; KANE M J, Breen P P, Quondamatteo F, ÓLaighin G. BION microstimulators: a case study in the engineering of an electronic implantable medical device. Med Eng Phys 33(January, 2011):7-16; U.S. Pat. No. 6,735,475, entitled Fully implantable miniature neurostimulator for stimulation as a therapy for headache and/or facial pain, to WHITEHURST et al]. In one nerve stimulation application, a BION device was found to be comparable in benefit to a noninvasive nerve stimulation device, but with the noninvasive device having the advantage of not needing to be implanted [A NESBITT, J Marin, P Goadsby. Treatment of hemicrania continua by non-invasive vagus nerve stimulation in 2 patients previously treated with occipital nerve stimulation. The Journal of Headache and Pain 1(Suppl 1, 2013):P230].

The BION device was developed in response to a request from the U.S. National Institutes of Health, and another such device was developed by ZIAIE and colleagues [ZIAIE B, Nardin M D, Coghlan A R, Najafi K. A single-channel implantable microstimulator for functional neuromuscular stimulation. IEEE Trans Biomed Eng 44(October, 1997):909-920; TROYK P R. Injectable electronic identification, monitoring, and stimulation systems. Annu Rev Biomed Eng 1(1999):177-209]. Subsequently, inductive micro-stimulators have been developed for additional applications [Rogier A M RECEVEUR, Fred W Lindemans and Nicolaas F de Rooij. Microsystem technologies for implantable applications. Journal of Micromechanics and Microengineering 17(May, 2007):R50-R80].

Microtransponder devices resemble human-implantable radiofrequency-identification microchips, which are powered inductively from an external electromagnetic field. They may be joined in arrays and delivered to the vicinity of a nerve through a hypodermic needle. One of their intended applications is the stimulation of a peripheral nerve [U.S. Pat. No. 7,630,771, entitled Grooved electrode and wireless microtransponder system, to CAULLER; US20050137652, entitled System and method for interfacing cellular matter with a machine, to CAULLER et al; US20090163889, entitled Biodelivery System for Microtransponder Array, to CAULLER et al; US20120296399, entitled Array of Joined Microtransponders for Implantation, to CAULLER et al; ROSELLINI W, Casavant R, Engineer N, Beall P, Pierce D, Jain R, Dougherty P M. Wireless peripheral nerve stimulation increases pain threshold in two neuropathic rat models. Exp Neurol 235(February, 2012):621-626; Sung-Hoon CHO, Lawrence Cauller, Will Rosellini, and J B Lee, A MEMS-Based Fully-Integrated Wireless neurostimulator, IEEE 23rd International Conference on Micro Electro Mechanical Systems (MEMS), 24-28 Jan. 2010, Hong Kong, Proceedings pp. 300-303].

There also exists an implanted, externally-powered nerve stimulation system that does not use coils to power the implant, but it contains a tethered lead implantation, and it also requires the source of power to be applied directly to the patient's skin. It works by using a pair of noninvasive electrodes applied to the patient's skin to cause currents to flow under the skin, such that some of this current passes through electrical conductors that had been implanted in the vicinity of the nerve that is to be stimulated [Patent application US 20130013041, entitled Implant system and method using implanted passive conductors for routing electrical current, to GLUKHOVSKY et al.; Liu Shi G A N, Einat N. Ravid, Jan Kowalczewski, Michel Gauthier, Jaret Olson, Michael Morhart and Arthur Prochazka. First permanent human implant of the Stimulus Router System, a novel neuroprosthesis: preliminary testing of a polarity reversing stimulation technique. Conf Proc IEEE Eng Med Biol Soc. 2011:3051-3054; Timothy R. DEER, Jason E. Pope, Matthew Kaplan. A novel method of neurostimulation of the peripheral nervous system: The StimRouter implantable device. Techniques in regional anesthesia and pain management 16 (2012):113-117].

To summarize the foregoing background information, one prefers an implanted peripheral nerve stimulator (for example, a vagus nerve stimulator) that can be powered using approximately plane wave or far-field electromagnetic waves with frequencies in the range of 300 MHz to 10 GHz, so that the antenna transmitting energy for the stimulator's electrodes does not have to be placed in close proximity to the implanted stimulator in order for the stimulator to receive the energy. A related preference is that the stimulator should have simple circuitry so as to consume a small amount of power, and also so that the external transmitter can be a relatively weak power source (either inherently or because it is positioned at some distance from the implanted stimulator). One also prefers an implanted stimulator that does not have attached cables or tubes, the tethering of which would cause chronic tissue response due to movement of tethering cables. That is to say, one prefers a miniature self-contained stimulator that can be powered by external GHz plane wave or far-field electromagnetic radiation, with small power requirements. Because some such devices could be implanted with minimally invasive methods, they have additional medical and cosmetic advantages over the implantation of a conventional vagus nerve stimulator through open neck surgery. This is because the standard surgical approach to placement of vagus nerve stimulator electrodes is through an incision in the neck, approximately 4 cm in length. In patients who have difficulty with keloid and painful scar formation, and for those patients who are resistant to a neck scar for cosmetic reasons, conventional vagus nerve stimulator therapy has little appeal, regardless of its effectiveness.

The present application discloses methods for solving these problems that arise in the design and implantation of a compact, remotely-powered vagus nerve stimulator. It also discloses new methods for selecting a percutaneous path along which the vagus nerve stimulator is implanted, for performing the implantation with the aid of a robot, for attaching the implant to surrounding tissue, for repositioning or rotating the implanted stimulator if that becomes necessary, and for monitoring the safety and success of the implant procedure.

SUMMARY

The present invention provides systems, apparatus and methods for selectively applying electrical energy to body tissue. In particular, the invention relates to the electrical stimulation of excitable tissue, such as a nerve or nerve ganglion, using devices that are preferably powered wirelessly. The stimulator uses an adjustable number of fixed voltage (or fixed current) pulses with fixed duration to elicit desired changes in nerve response, the timing of which are controlled by an external power transmitter and controller.

In certain embodiments, methods are provided to apply an electrical impulse to modulate, stimulate, inhibit or block electrical signals in nerves within or around the carotid sheath, to acutely treat a condition or symptom of a patient. In certain preferred embodiments, the electrical signal may be adapted to reduce, stimulate, inhibit or block electrical signals in a vagus nerve to treat many conditions, such as hypotension associated with sepsis or anaphylaxis, hypertension, diabetes, bronchoconstriction, hypovolemic shock, asthma, sepsis, epilepsy, depression, obesity, gastroparesis, anxiety disorders, primary headaches, such as migraines or cluster headache, Alzheimer's disease and any other ailment affected by vagus nerve transmissions. Such conditions or symptoms are described in co-pending, commonly assigned patent applications listed in the section Cross Reference to Related Applications, the complete disclosures of which have already been incorporated herein by reference.

In one aspect of the invention, a stimulation device comprises one or more electrodes and a pulse generator. The pulse generator is configured to generate an electrical impulse having a fixed amplitude (either fixed voltage or fixed current) and a variable duration. The electrical impulse is applied through the electrodes to excitable tissue, such as nerve or nerve ganglions, to modulate that tissue. In a preferred embodiment, the duration of the electrical impulse is varied by varying a number of fixed-duration, fixed-amplitude pulses that are applied within each electrical impulse. Varying the number of these fixed-amplitude pulses allows the stimulation device to apply an electrical impulse that will cause the nerve to reach its threshold potential without varying the amplitude of the electrical impulse.

The stimulator circuit is novel in that it removes one or more elements from conventional stimulators, without sacrificing performance. In particular, the present invention removes from conventional designs the ability of the stimulator to vary the amplitude of the stimulation pulses. Unexpectedly, one can get substantially the same stimulatory effect as that provided by conventional stimulators, by keeping waveform parameters fixed, particularly the amplitude of the electrical impulse, but by then controlling the number and timing of pulses that the nerve experiences, in order to achieve the same physiologically desirable level of nerve stimulation. In essence, this invention uses an adjustable number of fixed voltage (or fixed current) pulses with fixed duration to elicit desired changes in nerve response. These fixed voltage pulses create one long continuous pulse to the nerve to ensure that sufficient energy is delivered to the nerve to cause the nerve to reach its action potential and fire. Thus, the present invention reaches the threshold energy level for a nerve to fire by adjusting the duration of the pulse received by the nerve, rather than adjusting the amplitude of the pulse.

In another aspect of the invention, the specific number of fixed amplitude pulses that will be delivered to the nerve is preferably determined through an iterative process with each patient. Once the surgeon determines the number of fixed voltage pulses required to stimulate the nerve for a particular patient, this number is programmed into either the external controller or the implantable stimulator.

In a preferred embodiment, the energy that is used to produce the impulses is received wirelessly by a dipole or other type of antenna that is also part of the stimulator. The received energy is preferably from far-field or approximately plane wave electromagnetic waves in the frequency range of about 0.3 to 10 GHz, more preferably about 800 MHz to 6 GHz and even more preferably about 800 MHz to 1.2 GHz. In an exemplary embodiment, the carrier signal is around 915 MHz. The electrical energy is transmitted from the antenna of an external energy source that is preferably a meter or more outside the patient, but that may also be situated closer or even be placed within the patient. In some embodiments, the transmitter may be worn around the neck as a pendant, placed in a pocket, attached to a belt or watch, or clipped to clothing. The transmitter of wireless power and control signals is preferably recharged at a recharging base station that may be positioned remotely from the implanted device, so that patients can sleep without having to wear the transmitter, even while the transmission is in progress The present invention provides an implanted peripheral nerve stimulator, such as a vagus nerve stimulator, that can be powered using approximately plane wave or far-field electromagnetic waves with frequencies in the range of 300 MHz to 10 GHz so that the antenna transmitting energy for the stimulator's electrodes does not have to be placed in close proximity to the implanted stimulator in order for the stimulator to receive the energy. In addition, the stimulation device has relatively simple circuitry so as to consume a small amount of power, and also so that the external transmitter can be a relatively weak power source (either inherently or because it is positioned at some distance from the implanted stimulator). In particular, the present invention is advantageous for vagus nerve stimulation because the stimulation device can be implanted with minimally invasive methods, For example, the stimulation device may be implanted through a percutaneous penetration in the neck.

In preferred embodiments of the present invention, the parameters of fixed stimulation pulses are generally as follows. The shape of the pulse is square, sine, triangular or trapezoidal with negative voltage return to eliminate DC bias. The electrical impulse will typically have a frequency of between about 1-500 Hz, preferably about 1 to 50 Hz, and more preferably about 10-35 Hz. In an exemplary embodiment, the frequency for the impulse received by the nerve is about 25 Hz. The preferred fixed voltage received by the nerve is between about 1-20 V and will typically vary depending on the size and type of electrode and the distance between the electrode and the nerve. In certain embodiments where the nerve is directly attached to the nerve (or implanted adjacent to the nerve), the fixed voltage is preferably about 1 to 4 volts, more preferably about 2 volts. In other embodiments, wherein the electrode is, for example, injected into the patient and implanted outside of the sheath, the voltage is preferably between about 7-15 volts and more preferably about 10 V. In embodiments wherein the current is fixed or held constant, the preferred fixed current is about 0.5 mA to about 20 mA. Similar to voltage, the fixed current will vary depending on the size and type of electrode and its distance from the nerve. In those embodiments where the electrode is adjacent to, or on, the nerve, the current is preferably about 0.5 to 5 mA and more preferably about 3.5 mA. In those embodiments, where the electrode is spaced from the nerve (just as an injectable electrode outside of the sheath), the current is preferably about 7-15 mA and more preferably about 10 mA. The pulse duration is preferably between about 50 to 1000 uS, more preferably about 100 to 400 uS and about 200 uS in an exemplary embodiment.

In another aspect of the invention, the stimulator circuit comprises either a battery or a storage device, such as a capacitor, for storing energy or charge and then delivering that charge to the circuit to enable the circuit to generate the electrical impulses and deliver those impulses to the electrodes. The energy for the storage device is preferably wirelessly transmitted to the stimulator circuit through a carrier signal from the external controller. In the preferred embodiments, the energy is delivered to the energy storage device between electrical impulses. Thus, the energy is not being delivered in "real-time", but during the periods when the pulse is not being delivered to the nerve or during the refractory period of the nerve. For example, a typical electrical impulse may be ON for about 200 uS and then OFF for about 39,000 uS. The energy is delivered during this longer OFF time, which enables the system to use a much smaller signal from the external generator. The external generator delivers the carrier signal over the OFF period to charge the energy storage device, which then releases this energy or charge to the remainder of the circuit to deliver the electrical impulse during the 200 uS ON time. This reduces the strength of the signal required to deliver the electrical energy to the storage device within the stimulator circuit because there is a longer period of time to deliver the energy. In addition, it enhances the safety of the device because it reduces the risk that uncontrolled environmental RF energy will create an electrical connection between the nerve and the charged energy.

In a preferred embodiment, the electrode and signal generator are primarily, but not exclusively, intended for stimulation of the vagus nerve in the neck, for conditions that include headache, epilepsy, asthma, anxiety/depression, gastric motility disorders, fibromyalgia, Alzheimer's disease, stroke, posttraumatic stress disorder, and traumatic brain injury. In those applications, the typical signal would be square or sine pulses of fixed amplitude of approximately 10 Volts, where each pulse has a fixed duration of 200 uS. Typically 5 of these pulses would be produced every 40 mS to produce an effective 25 Hz signal.

The electrical impulse is sufficient to modulate a selected nerve (e.g., vagus or one of its branches) at or near the target region to treat a condition or symptom of the patient. The stimulator is configured to induce a peak pulse voltage sufficient to produce an electric field in the vicinity of the nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m (preferably less than 100 V/m) and/or an electrical field gradient of greater than 2 V/m/mm. Electric fields that are produced at the vagus nerve are generally sufficient to excite all myelinated A and B fibers, but not necessarily the unmyelinated C fibers. However, by using a suitable amplitude of stimulation, excitation of A-delta and B fibers may also be avoided.

The stimulation device may be implanted within a patient by open, endoscopic or minimally invasive methods. In a preferred embodiment, the stimulator is introduced through a percutaneous penetration in the patient to a target location within, adjacent to, or in close proximity with, the carotid sheath that contains a vagus nerve. Once in position, electrical impulses are applied through the electrodes of the stimulator to one or more selected nerves (e.g., vagus nerve or one of its branches) to stimulate, block or otherwise modulate the nerve(s) and treat the patient's condition or a symptom of that condition. For some conditions, the treatment may be acute, meaning that the electrical impulse immediately begins to interact with one or more nerves to produce a response in the patient. In some cases, the electrical impulse will produce a response in the nerve(s) to improve the patient's condition or symptom in less than 3 hours, preferably less than 1 hour and more preferably less than 15 minutes. For other conditions, intermittent scheduled or as-needed stimulation of the nerve may produce improvements in the patient over the course of several days or weeks.

A system for implanting the stimulator preferably includes an introducer for creating percutaneous access to the target region. The introducer may include an access device such as a finder needle for creating percutaneous access through a skin surface of the patient's neck, and a cannula having an inner lumen for passage of the stimulator there through. The access device, e.g. finder needle, is introduced through the patient's skin surface in the neck and advanced to a target location, ordinarily near a vagus nerve. The target location may be within, directly adjacent to, or in contact with the carotid sheath, or it may be in close proximity with (e.g., within 1-5 mm) of the carotid sheath. The preferred target location, as well as the preferred path that the finder needle takes to that location, will depend on several factors. They include the length of the stimulator and the number of its electrodes, whether the stimulator's electrodes should produce an electric field that is intended to have particular directionality, whether deployable anchoring attachments will be used to secure the stimulator to particular surrounding tissue, as well as consideration of the electrical waveforms that may be used to preferentially stimulate the vagus nerve (including the maximum strength or amplitude of the stimulus), the likelihood that the other structures will not be damaged during the implantation or eventually co-stimulated, and the ease with which the finder needle may penetrate and actually follow the intended path.

Before deciding the target location and path, ultrasound imaging of the patient's neck region is performed by the surgeon, preferably in three dimensions and with color flow Doppler in conjunction with microbubbles used as a contrast agent. Objects identified by such imaging would preferably include the vagus nerve and its position within the carotid sheath, large and small blood vessels, cervical sympathetic ganglia, and the phrenic nerve. Insertion of the finder needle to the target location along the preferred anatomical path may be performed by a robotic device comprising the finder needle that is positioned under computer control by actuators, as well as a force sensor and an ultrasound transducer that provide data used to generate feedback control of the robot.

Once the finder needle is in position, the electrical stimulator is advanced to the target location and secured in position. In certain embodiments, a cannula or similar device is first advanced to the target region, and the electrical stimulator is then directed through the cannula. Insertion of the stimulator to the target location may be accomplished by forcing tubing attached to the tail of the stimulator through the cannula. Electrical stimulation of the nerve is then performed, and tests are made to verify that the stimulator is working as intended. For example, the patient may be requested to vocalize a vowel such as /a/ over several voice ranges (continuous glissando) with and without stimulation. An acoustic analysis of the vocalization may be used to decide whether electrical stimulation of the vagus nerve by electrodes of the implanted stimulator is in fact having an effect. In preferred embodiments, the tubing is then detached from the stimulator, and the tubing and cannula are withdrawn. In some embodiments, anchoring of the stimulator to surrounding tissue is made by deployable springs or by inflatable anchoring attachments. In one embodiment, repositioning of the stimulator after it has been implanted may be accomplished with an external magnetic field acting on a permanent magnet or soft-magnetic material that is part of the stimulator.

In one embodiment, the electrical stimulator comprises an active and a return electrode located on the stimulator body. In this embodiment, an electrical impulse is applied across the active and return electrodes such that the electric current is generally confined within a local space around the electrical stimulator (i.e., a bipolar electrode configuration), which may be in a particular direction (directed towards the nerve) for some electrode configurations.

The novel systems, devices and methods of the present invention are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 1A is a schematic view of a nerve modulating system (implantable lead module or electrical stimulator) according to one or more aspects of the present invention.

FIG. 1B is a schematic view of an implantable stimulation device according to the present invention.

FIG. 2A illustrates one embodiment of an electrode assembly in an implantable stimulation device according to the present invention.

FIG. 2B-2F illustrate additional embodiments of electrode assemblies according to the present invention.

FIG. 3 illustrates the vertebrae and major vessels of the neck, including the carotid sheath (FIG. 3A), as well as muscles that lie in the vicinity of those vessels (FIGS. 3B and 3C).

FIG. 7 illustrates an embodiment of the stimulator that is designed to implant electrodes parallel to a nerve by rotating the electrodes about a hinge, as well as to anchor the stimulator to structures within the patient's neck, in which anchoring ribbon springs that had been folded against tubing are released in order to hug surrounding tissue.

FIG. 8 illustrates an embodiment of the stimulator that is designed to be implanted parallel to a nerve and to anchor the stimulator to structures within the patient's neck, comprising an anchoring ribbon spring that is initially coiled around tubing before being released in order to hug surrounding tissue.

DETAILED DESCRIPTION

Figure 1C:
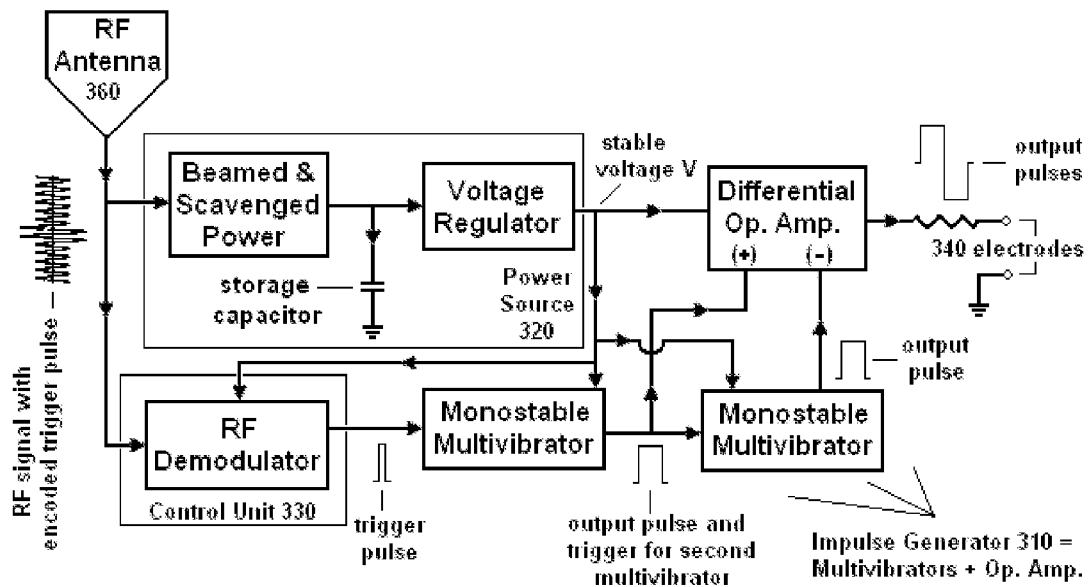
FIG. 1C is a more specific view of the components of one embodiment of the implantable stimulation device of FIG. 1B.

In one or more embodiments of the present invention, electrical energy is applied in a patient to a target region within or around the carotid sheath (also called the carotid neurovascular bundle) to treat a patient's ailment. The invention is particularly useful for applying electrical impulses that ultimately interact with the signals of a vagus nerve, which lies within the carotid sheath, to achieve a therapeutic result. The nerve stimulation may result in benefits to the patient such as: relaxation of the smooth muscle of the bronchia, increase in blood pressure associated with orthostatic hypotension, reduction in blood pressure, treatment of epilepsy, treating ileus conditions, depression, anaphylaxis, obesity, a neurodegenerative disorder such as Alzheimer's disease, migraine and other types of headache, rhinitis, sinusitis, asthma, atrial fibrillation, autism, gastroparesis and other functional gastrointestinal disorders, and/or any other ailment that may be affected by nerve transmissions of a vagus nerve. Such treatments for different disorders are disclosed in the commonly-assigned applications that are listed in the section Cross Reference to Related Applications of this disclosure.

The fact that electrical stimulation of a vagus nerve can be used to treat so many disorders may be understood as follows. The vagus nerve is composed of motor and sensory fibers. The vagus nerve leaves the cranium, passes down the neck within the carotid sheath to the root of the neck, then passes to the chest and abdomen, where it contributes to the innervation of the viscera. A human vagus nerve (tenth cranial nerve, paired left and right) consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system.

The largest nerve fibers within a left or right vagus nerve are approximately 20 μm in diameter and are heavily myelinated, whereas only the smallest nerve fibers of less than about 1 μm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 μm diameter), A-beta fibers (afferent or efferent fibers, 5-12 μm), A-gamma fibers (efferent fibers, 3-7 μm), A-delta fibers (afferent fibers, 2-5 μm), B fibers (1-3 μm) and C fibers (unmyelinated, 0.4-1.2 μm). The diameters of group A and group B fibers include the thickness of the myelin sheaths.

The vagus (or vagal) afferent nerve fibers arise from cell bodies located in the vagal sensory ganglia, which take the form of swellings near the base of the skull. Vagal afferents traverse the brainstem in the solitary tract, with some eighty percent of the terminating synapses being located in the nucleus of the tractus solitarius (or nucleus tractus solitarii, nucleus tractus solitarius, or NTS). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(May, 1991):A3-A52]. Thus, stimulation of vagal afferents can modulate the activity of many structures of the brain and brainstem through these projections.

With regard to vagal efferent nerve fibers, two vagal components have evolved in the brainstem to regulate peripheral parasympathetic functions. The dorsal vagal complex, consisting of the dorsal motor nucleus and its connections controls parasympathetic function primarily below the level of the diaphragm, while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

The vagus efferent fibers innervate parasympathetic ganglionic neurons that are located in or adjacent to each target organ. The vagal parasympathetic tone resulting from the activity of these fibers is balanced reflexly in part by sympathetic innervations. Consequently, electrical stimulation of a vagus nerve may result not only in modulation of parasympathetic activity in postganglionic nerve fibers, but also a reflex modulation of sympathetic activity. The ability of a vagus nerve to bring about widespread changes in autonomic activity, either directly through modulation of vagal efferent nerves, or indirectly via activation of brainstem and brain functions that are brought about by electrical stimulation of vagal afferent nerves, accounts for the fact that vagus nerve stimulation can treat many different medical conditions in many end organs. Selective treatment of particular conditions is possible because the parameters of the electrical stimulation (frequency, amplitude, pulse width, etc.) may selectively activate or modulate the activity of particular afferent or efferent A, B, and/or C fibers that result in a particular physiological response in each individual.

As ordinarily practiced, the electrodes used to stimulate a vagus nerve are implanted about the nerve during open neck surgery. For many patients, this may be done with the objective of implanting permanent electrodes to treat epilepsy, depression, or other conditions [Arun Paul AMAR, Michael L. Levy, Charles Y. Liu and Michael L. J. Apuzzo. Chapter 50. Vagus nerve stimulation. pp. 625-638, particularly 634-635. In: Elliot S. Krames, P. Hunber Peckham, Ali R. Rezai, eds. Neuromodulation. London: Academic Press, 2009; KIRSE D J, Werle A H, Murphy J V, Eyen T P, Bruegger D E, Hornig G W, Torkelson R D. Vagus nerve stimulator implantation in children. Arch Otolaryngol Head Neck Surg 128(November, 2002):1263-1268]. In that case, the electrode is often a spiral electrode, although other designs may be used as well [U.S. Pat. No. 4,979,511, entitled Strain relief tether for implantable electrode, to TERRY, Jr.; U.S. Pat. No. 5,095,905, entitled Implantable neural electrode, to KLEPINSKI]. In other patients, a vagus nerve is electrically stimulated during open-neck thyroid surgery in order to confirm that the nerve has not been accidentally damaged during the surgery. In that case, a vagus nerve in the neck is surgically exposed, and a temporary stimulation electrode is clipped about the nerve [SCHNEIDER R, Randolph G W, Sekulla C, Phelan E, Thanh P N, Bucher M, Machens A, Dralle H, Lorenz K. Continuous intraoperative vagus nerve stimulation for identification of imminent recurrent laryngeal nerve injury. Head Neck. 2012 Nov. 20. doi: 10.1002/hed.23187 (Epub ahead of print, pp. 1-8)].

In a commonly assigned, copending application, Applicant disclosed that it is also possible to electrically stimulate a vagus nerve using a minimally invasive surgical approach, namely percutaneous nerve stimulation. In that procedure, a pair of electrodes (an active and a return electrode) are introduced through the skin of a patient's neck to the vicinity of a vagus nerve, and wires connected to the electrodes extend out of the patient's skin to a pulse generator [Publication number US20100241188, entitled Percutaneous electrical treatment of tissue, to J. P. ERRICO et al.; SEPULVEDA P, Bohill G, Hoffmann T J. Treatment of asthmatic bronchoconstriction by percutaneous low voltage vagal nerve stimulation: case report. Internet J Asthma Allergy Immunol 7(2009):e1 (pp 1-6); MINER, J. R., Lewis, L. M., Mosnaim, G. S., Varon, J., Theodoro, D. Hoffman, T. J. Feasibility of percutaneous vagus nerve stimulation for the treatment of acute asthma exacerbations. Acad Emerg Med 2012; 19: 421-429].

Percutaneous nerve stimulation procedures had previously been described primarily for the treatment of pain, but not for a vagus nerve, which is ordinarily not considered to produce pain and which presents special challenges [HUNTOON M A, Hoelzer B C, Burgher A H, Hurdle M F, Huntoon E A. Feasibility of ultrasound-guided percutaneous placement of peripheral nerve stimulation electrodes and anchoring during simulated movement: part two, upper extremity. Reg Anesth Pain Med 33(June, 2008):558-565; CHAN I, Brown A R, Park K, Winfree C J. Ultrasound-guided, percutaneous peripheral nerve stimulation: technical note. Neurosurgery 67(3 Suppl Operative, 2010):ons136-139; MONTI E. Peripheral nerve stimulation: a percutaneous minimally invasive approach. Neuromodulation 7(March, 2004):193-196; Konstantin V SLAVIN. Peripheral nerve stimulation for neuropathic pain. US Neurology 7(February, 2011):144-148].

In the present invention, electrodes are preferably also introduced percutaneously to the vicinity of a vagus nerve, but unlike the previous minimally invasive disclosure, the electrodes are not ultimately connected to wires that extend outside the patient's skin. Instead, in the present invention, the percutaneously implanted stimulator receives energy wirelessly from an external transmitter that need not be in close proximity to the skin of the patient, and electrical pulse generation occurs within the implanted stimulator using that energy.

As shown in FIG. 1A, the nerve modulating device 300 of the present invention (also known as an implantable lead module or simply an electrical nerve stimulator) is powered by the receipt of far-field or approximately plane wave electromagnetic energy with frequencies in the range of 0.3 to 10 GHz (preferably about 800 MHz to about 6 GHz, and more preferably about 800 MHz to about 1.2 MHz) which is received wirelessly by an antenna 360 within, or attached to, the device 300. The energy that powers the nerve modulating device 300 is transmitted by an external device, which in FIG. 1A is labeled as a Controller 370. Controller 370 is in turn controlled by a programmer device 380, which preferably communicates with controller 370 wirelessly. In operation, the nerve modulating device 300 is implanted within the patient, the controller 370 may be either outside of the patient or implanted within the patient, and the programmer 380 is operated manually by the patient or a caregiver. The antenna of the controller 370 is actively tuned/matched to the resonant frequency of an antenna in the implanted device 300 so that the maximum efficiency of power transmission is achieved. There may be several antennae at various orientations in the external unit and/or in the implanted signal generator to enhance coupling efficiency in various orientations. The unit 370 supplying power and control to the implanted device 300 could be AC powered and/or battery powered. If powered by rechargeable batteries, a battery charger may be an accessory to the system. The controller 370 is preferably both portable and rechargeable. In one embodiment, it may be worn around the neck as a pendant, placed in a pocket, or clipped to clothing. This wireless transmitter 370 is preferably recharged at a recharging base and has a significant range of transmission, preferably up to four feet, so that patients can sleep without having to wear the transmitter.

FIG. 1B is a more detailed schematic diagram of the nerve modulating device 300 for delivering electrical impulses to nerves. As shown, device 300 comprises an electrical impulse generator 310; a power source 320 coupled to the electrical impulse generator 310; a control unit 330 in communication with the electrical impulse generator 310 and coupled to the power source 320; and one or more electrodes 340 coupled to the electrical impulse generator 310. Nerve modulating device 300 is configured to generate electrical impulses sufficient to modulate the activity of one or more selected regions of a nerve (not shown). The power source 320 receives energy wirelessly via an antenna 360, wherein the energy is in the form of far-field or approximately plane-wave electromagnetic waves with frequencies in the range of 0.3 to 10 GHz, preferably about 800 MHz to about 1.2 MHz.

The control unit 330 may control the electrical impulse generator 310 for generation of a signal suitable for amelioration of a patient's condition when the signal is applied via the electrodes 340 to the nerve. It is noted that nerve modulating device 300 excluding the electrodes 340 may be referred to by its function as a pulse generator. U.S. Patent Application Publications 2005/0075701 and 2005/0075702, both to SHAFER, both of which are incorporated herein by reference, relating to stimulation of neurons of the sympathetic nervous system to attenuate an immune response, contain descriptions of pulse generators that may be applicable to various embodiments of the present invention.

FIG. 1C illustrates one embodiment of the nerve modulating device 300 that consumes relatively little power and may therefore receive power from a correspondingly weak and/or distant external transmitter. To achieve low power consumption, the embodiment is designed to use a minimum of components. This may be accomplished by designing the device to produce constant voltage pulses, rather than constant current pulses, because circuits for the latter are more complex and consume more power than the former. However, for some patients a constant current pulse may be preferred, depending on the detailed anatomy of the patient's neck in the vicinity of the stimulated nerve (see below and FIG. 4). Consequently, constant current pulses are also contemplated by the invention [DELIMA, J. A. and Cordeiro, A. S. A simple constant-current neural stimulator with accurate pulse-amplitude control. Engineering in Medicine and Biology Society, 2001. Proceedings of the 23rd Annual International Conference of the IEEE (Vol. 2, 2001) 1328-1331]. In either case, simplicity of circuit design is provided by a design that makes the amplitude of the pulse constant, rather than by allowing the amplitude to be variable. Accordingly, the present invention modulates the stimulation power to the nerve by altering the number and timing of the pulses, rather than by modulating the amplitude of individual pulses. Additional simplicity of design may be achieved by using communication that occurs in one direction only, from the transmitter to the stimulator (simplex communication according to the ANSI definition, rather than half or full duplex communication).

The stimulator circuit is novel in that it removes one (or more) elements from conventional stimulators, without sacrificing performance. In particular, the present invention removes from conventional designs the ability of the stimulator to vary the amplitude of the stimulation pulses. Unexpectedly, one can get substantially the same stimulatory effect as that provided by conventional stimulators, by keeping waveform parameters fixed, particularly the amplitude of pulses, but by then controlling the number and timing of pulses that the nerve experiences, in order to achieve the same physiologically desirable level of nerve stimulation. In essence, this invention uses an adjustable number of fixed voltage (or fixed current) pulses with fixed duration to elicit desired changes in nerve response. These fixed voltage pulses create one long continuous pulse to the nerve to ensure that sufficient energy is delivered to the nerve to cause the nerve to reach its action potential and fire. Thus, the present invention reaches the threshold energy level for a nerve to fire by adjusting the duration of the pulse received by the nerve, rather than adjusting the amplitude of the pulse.

In another aspect of the invention, the specific number of fixed amplitude pulses that will be delivered to the nerve is preferably determined through an iterative process with each patient. Once the surgeon determines the number of fixed voltage pulses required to stimulate the nerve for a particular patient, this number is programmed into either the external controller or the implantable stimulator.

A constant-voltage pulse design teaches against prevailing preferred designs for vagus nerve stimulators. Thus, constant-voltage pulses are used in cardiac pacemakers, deep brain stimulation, and some implantable neuromodulators for treatment of incontinence and chronic pain, but constant-current pulses are used for cochlear implants and vagus nerve stimulators [D. PRUTCHI and M. Norris Stimulation of excitable tissues. Chapter 7, pp. 305-368. In: Design and development of medical electronic instrumentation. Hoboken: John Wiley & Sons, 2005]. In the latter applications, the constant current design is said to be preferred becauses light variations in stimulator-to-nerve distance change the ability of the constant-voltage pulse stimulator to depolarize the nerve, which is less of a problem with constant-current pulse stimulators. With the constant current design, the stimulation thresholds stay more or less constant even with changing electrode impedance and in growth of tissue into the neural interface [Emarit RANU. Electronics. Chapter 10, pp. 213-243. In: Jeffrey E. Arle, Jay L. Shils(eds). Essential Neuromodulation. Amsterdam, Boston: Academic Press. 2011]. For example, the BION stimulators described in the background section of the present application generate only constant current pulses.

In some embodiments of the present invention, a constant voltage pulse is used because it can be produced with a simpler circuit that consumes less power, as compared with constant pulse current circuits. The above-mentioned potential problem with variation in stimulator-to-nerve distance is addressed by anchoring the stimulator to the vagus nerve (see FIGS. 7 and 8). Furthermore, the problem may be circumvented to some extent in the present invention by coating the stimulator's electrodes with a very thin layer of poorly conducting material. This is because the presence of a poorly conducting boundary layer surrounding the stimulator minimizes the differential effects of conductivity variations and electrode location during constant current and constant voltage stimulation[Mark M. STECKER. Nerve stimulation with an electrode of finite size: differences between constant current and constant voltage stimulation. Computers in Biology and Medicine 34(2004):51-94].

Additional circuit simplicity and minimized power requirements are accomplished in the embodiment shown in FIG. 1C by fixing the characteristics of the stimulation pulses, rather than by adding circuits that would allow the characteristics to be adjusted through use of external control signals. For example, the output pulses shown in FIG. 1C are shown to be generated using a pair of monostable multivibrators. The first multivibrator receives a trigger pulse from the control unit 330, resulting in a pulse of fixed duration. The second multivibrator is triggered by the falling edge of the first multivibrator's pulse, and the pair of pulses from the two multivibrators are combined with suitable polarity using a differential operational amplifier. Thus, in this example, the impulse generator 310 consists of the multivibrators and operational amplifier. The amplifier in turn presents the stimulation pulses to the electrodes 340. The time period that a monostable multivibrator remains in its unstable state (the pulse width) is a function of its component resistor and capacitor values, so if the pulse width can be preselected for a patient, the device can be designed using correspondingly fixed R and C values. On the other hand, if a variable pulse width is needed during preliminary testing with a patient, the multivibrator circuit can be made more complex, with the pulse width selected on the basis of coded signals that are transmitted to the impulse generator 310 via the control unit 330. Once the appropriate pulse width has been selected, a control signal may be sent from the control unit 330 to disable extraneous power consumption by the variable pulse-width circuitry. Proper pulse width is particularly important in stimulating nerve fibers having the appropriate diameters [see discussion below and SZLAVIK R B, de Bruin H. The effect of stimulus current pulse width on nerve fiber size recruitment patterns. Med Eng Phys 21(June-July, 1999):507-515].

It is also understood that more complex pulses may also be preferred, as illustrated below in FIG. 5, which would require a correspondingly more complex circuitry and possibly additional power consumption, as compared with the circuit shown in FIG. 1C [JEZERNIK S, Morari M. Energy-optimal electrical excitation of nerve fibers. IEEE Trans Biomed Eng 52(April, 2005):740-743; Wongsarnpigoon A, Woock J P, Grill W M. Efficiency analysis of waveform shape for electrical excitation of nerve fibers. IEEE Trans Neural Syst Rehabil Eng 18(March, 2010):319-328; FOUTZ T J, Ackermann D M Jr, Kilgore K L, McIntyre C C (2012) Energy efficient neural stimulation: coupling circuit design and membrane biophysics. PLoS ONE 7(12): e51901. doi:10.1371/journal.pone.0051901, pp. 1-8; McLEOD KJ, Lovely D F, Scott R N. A biphasic pulse burst generator for afferent nerve stimulation. Med Biol Eng Comput 25(January, 1987):77-80].

The control unit 330 in FIG. 1C is shown to exercise its control only by presenting trigger pulses to the impulse generator 310. In this example, the train of pulses appearing across the electrodes 340 is determined only by the timing of the sequence of trigger pulses. The trigger pulses are themselves encoded in the signal that is transmitted from controller 370 in FIG. 1A, shown in FIG. 1C as "RF signal with encoded trigger pulse." The trigger pulses are extracted and reconstructed from the transmitted signal by an RF demodulator in the control unit 330. There are many methods for transmitting and decoding such control signals, and the present invention may be designed to use any of them [Robert PUERS and Jef Thoné. Short distance wireless communications. Chapter 7, pp. 219-277, In: H.-J. Yoo, C. van Hoof (eds.), Bio-Medical CMOS ICs. New York: Springer, 2011]. Because the timing of pulses is determined by the trigger pulses emanating from the transmitted signal, the circuit shown in FIG. 1C does not even need a clock, thereby reducing its power requirements. However, in other embodiments a clock may be included as part of the timing circuitry. It is understood that in order to command a pulse of the treatment signal and switch that pulse to the electrodes, it is possible to use a control RF signal having a different frequency than the one used to provide power, or encode the command based on variation in the RF signal's amplitude, pulse width and/or duration.

The transmitted RF signal is received by an antenna 360, and the signal provides power for the stimulation device 300, in addition to the control signals. The power is provided by the power source 320 in FIG. 1C. As shown there, energy from the transmitted RF signal (beamed power) is accumulated in a storage capacitor, which is eventually discharged in conjunction with the creation of stimulation pulses that are applied to the electrodes 340. In addition to the beamed power, there may also be scavenged power, which arises from the reception of ambient electromagnetic radiation by the antenna 360. Special circuits and antennas may be used to scavenge such ambient electromagnetic radiation [Soheil RADIOM, Majid Baghaei-Nejad, Guy Vandenbosch, Li-Rong Zheng, Georges Gielen. Far-field RF Powering System for RFID and Implantable Devices with Monolithically Integrated On-Chip Antenna. In: Proc. Radio Frequency Integrated Circuits Symposium (RFIC), 2010 IEEE, Anaheim, Calif., 23-25 May 2010, pp. 113-116]. Power scavenging may be most appropriate in a hospital setting where there is significant ambient electromagnetic radiation, due to the use thereof diathermy units and the like [FLODERUS B, Stenlund C, Carlgren F. Occupational exposures to high frequency electromagnetic fields in the intermediate range (>300 Hz-10 MHz). Bioelectromagnetics 23(August, 2002):568-577].

The stimulator circuit comprises either a battery or a storage device, such as a capacitor, for storing energy or charge and then delivering that charge to the circuit to enable the circuit to generate the electrical impulses and deliver those impulses to the electrodes. The energy for the storage device is preferably wirelessly transmitted to the stimulator circuit through a carrier signal from the external controller. In the preferred embodiments, the energy is delivered to the energy storage device between electrical impulses. Thus, the energy is not being delivered in "real-time", but during the periods when the pulse is not being delivered to the nerve or during the refractory period of the nerve. For example, a typical electrical impulse may be ON for about 200 uS and then OFF for about 39,000 uS. The energy is delivered during this longer OFF time, which enables the system to use a much smaller signal from the external generator. The external generator delivers the carrier signal over the OFF period to charge the energy storage device, which then releases this energy or charge to the remainder of the circuit to deliver the electrical impulse during the 200 uS ON time.

Transmitting energy to the storage device in between the electrical impulses provides a number of advantages. First, it increase the length of time that the electrical energy can be delivered to charge the storage device. This reduces the strength of the signal required to deliver the electrical energy to the storage device, thereby reducing the overall power requirements of the external controller and reducing the complexity of the stimulator circuitry. In addition, it enhances the safety of the device because it reduces the risk that uncontrolled environmental RF energy will create an electrical connection between the nerve and the charged energy. Since the storage device is receiving electrical energy between electrical impulses, there is no electrical connection between the stimulator circuit and the nerve as the storage device is charged. This reduces the risk of the electrical energy being accidentally applied to the nerve.

In order to power the impulse generator and demodulation circuits, the power source 320 in FIG. 1C makes use of a voltage regulator, the output from which is a stable voltage V. The circuits that may be selected for the voltage regulator comprise those described by BOYLESTAD [Robert L BOYLESTAD and Louis Nashelsky. Power Supplies (Voltage Regulators). Chapter 18, pp. 859-888. In: Electronic devices and circuit theory, 8th ed. Upper Saddle River, N.J.: Prentice Hall, 2002]

In preferred embodiments of the present invention, the parameters of fixed stimulation pulses are generally as follows. The shape of the pulse is square, sine, triangular or trapezoidal with negative voltage return to eliminate DC bias. The electrical impulse will typically have a frequency of between about 1-500 Hz, preferably about 1 to 50 Hz, and more preferably about 10-35 Hz. In an exemplary embodiment, the frequency for the impulse received by the nerve is about 25 Hz. The preferred fixed voltage received by the nerve is between about 1-20 V and will typically vary depending on the size and type of electrode and the distance between the electrode and the nerve. In certain embodiments where the nerve is directly attached to the nerve (or implanted adjacent to the nerve), the fixed voltage is preferably about 1 to 4 volts, more preferably about 2 volts. In other embodiments, wherein the electrode is, for example, injected into the patient and implanted outside of the sheath, the voltage is preferably between about 7-15 volts and more preferably about 10 V. In embodiments wherein the current is fixed or held constant, the preferred fixed current is about 0.5 mA to about 20 mA. Similar to voltage, the fixed current will vary depending on the size and type of electrode and its distance from the nerve. In those embodiments where the electrode is adjacent to, or on, the nerve, the current is preferably about 0.5 to 5 mA and more preferably about 3.5 mA. In those embodiments, where the electrode is spaced from the nerve (just as an injectable electrode outside of the sheath), the current is preferably about 7-15 mA and more preferably about 10 mA. The pulse duration is preferably between about 50 to 1000 uS.

Benefits of the disclosed system include the following features. The implanted signal generator can be much smaller than a traditional implanted generator. The surgery to implant this system can be done under local anesthesia on an outpatient basis in a non-hospital setting resulting in faster recovery and less scarring. Furthermore, since there is no implanted battery, the patient does not need additional surgeries to replace batteries, which is especially important if the patient has a treatment protocol that requires treatments involving significant power and duration. Also, the limited circuitry implanted in the body will be more reliable than traditional implanted generators. Because the treatment is powered and controlled from outside the body, changes to the treatment protocol can be made quickly and easily. In the event of an emergency, the patient or caregiver can quickly turn-off or remove the power/control unit to stop treatment.

The stimulator circuit is novel in that it removes one (or more) elements from conventional stimulators, without sacrificing performance. In particular, the present invention removes from conventional designs the ability of the stimulator to vary the amplitude of the stimulation pulses. Unexpectedly, one can get substantially the same stimulatory effect as that provided by conventional stimulators, by keeping waveform parameters fixed, particularly the amplitude of pulses, but by then controlling the number and timing of pulses that the nerve experiences, in order to achieve the same physiologically desirable level of nerve stimulation. In essence, this invention is using an adjustable number of fixed voltage (or current) pulses with fixed duration to elicit desired changes in nerve response.

The electrode and signal generator are primarily, but not exclusively, intended for stimulation of the vagus nerve in the neck, for conditions that include headache, epilepsy, asthma, anxiety/depression, gastric motility disorders, fibromyalgia, Alzheimer's disease, stroke, posttraumatic stress disorder, and traumatic brain injury. In those applications, the typical signal would be square or sine pulses of fixed amplitude approximately 2 Volts, where each pulse has a fixed duration of 200 uS. Typically 5 of these pulses would be produced every 40 mS to produce an effective 25 Hz signal. The selection of these waveform parameters is discussed more fully below.

Although the preferred embodiments of the invention are as described above, it is understood that one may also modify the capabilities of the device as follows. Optionally, the pulse command could have an address or other identifier associated with it so that only a particular signal generator would be activated. This would allow a patient to have multiple implanted signal generators in the body with each responding to its own command from the same or multiple power/control units. Another option would be to have circuitry or a processor in the implanted signal generator that could communicate a signal back to the power/control unit. This signal could contain status information such as voltage, current, number of pulses applied or other applicable data. The antennae and RF signals in this system could also be replaced by closely coupled coils of wire and lower frequency signals that are inductively coupled through the body.

No previous study has documented a need for more than a simple dipole configuration for percutaneous nerve stimulation, i.e., a configuration consisting of an electrode pair—a return and active electrode. Accordingly, the electrodes 340 in FIG. 1B may in one embodiment be simply such an electrode pair. Preferably, the pair of electrodes will be oriented parallel to the nerve, but a perpendicular (transverse) placement of the two electrodes in relation to the nerve might also provide acceptable stimulation [HUNTOON M A, Hoelzer B C, Burgher A H, Hurdle M F, Huntoon E A. Feasibility of ultrasound-guided percutaneous placement of peripheral nerve stimulation electrodes and anchoring during simulated movement: part two, upper extremity. Reg Anesth Pain Med 33(June, 2008):558-565].

Nevertheless, some investigators have adopted the use of three electrodes to stimulate a vagus nerve during surgical monitoring, on the grounds that stray currents are thereby minimized [V3 Vagus Electrode. Inomed North America. 453 Washington Street Suite 5A. Boston, Mass. 02111; LAMADE W, Ulmer C, Seimer A, et al. A new system for continuous recurrent laryngeal nerve monitoring. Minim Invasive Ther AlliedTechnol 16(2007):149-154; LAMADE W, Ulmer C, Rieber F, Friedrich C, Koch K P, Thon K P. New backstrap vagus electrode for continuous intraoperative neuromonitoring in thyroid surgery. Surg Innov 18(March, 2011):206-213; W. LAMADE, C. Ulmer, C. Friedrich, F. Rieber, K. Schymik, H. M. Gemkow, K. P. Koch, T. Göttsche, K. P. Thon. Signalstabilität als Grundvoraussetzung für kontinuierliches intraoperatives Neuromonitoring (Signal stability as key requirement for continuous intraoperative neuromonitoring). Chirurg 82(2011):913-920]. Accordingly, the electrodes 340 in FIG. 1B may in one embodiment comprise three electrodes.

Stimulation devices containing four or more electrodes are also contemplated by the invention. Such an electrode configuration would resemble the ones used for spinal cord stimulation, which provide rectangular, biphasic, charge-balanced pulses of adjustable rate and duration to each electrode. When used with a conventional pulse generator for such devices, all electrode contacts connected as anodes will have the same voltage, and all electrode contacts connected as cathodes will have the same voltage. Unipolar stimulation can be applied only if the device were to be connected with an insulated wire to a return electrode that is located distantly near the surface of the patient's skin. Thus, for devices containing four or more electrodes, each electrode is conventionally programmed to have one of three states: disconnected, anode, or cathode [DE VOS C C, Hilgerink M P, Buschman H P, Holsheimer J. Electrode contact configuration and energy consumption in spinal cord stimulation. Neurosurgery 65(6 Suppl, 2009):210-216].

For a device containing 16 or 32 electrodes, the number of possible programmed states is very large, in which case, the selection of the programmed state is preferably done by computer simulation [HOLSHEIMER J. Computer modelling of spinal cord stimulation and its contribution to therapeutic efficacy. Spinal Cord 36(August, 1998):531-540]. For the present invention, such computer modeling would incorporate knowledge of the electrical properties of the vagus nerve and its surrounding tissue. Pulse width is usually set to between 100 to 400 microseconds, but for such modeling, the pulse width is also a variable, which affects the area of coverage [LEE D, Hershey B, Bradley K, Yearwood T. Predicted effects of pulse width programming in spinal cord stimulation: a mathematical modeling study. Med Biol Eng Comput 49(July, 2011):765-774]. The result of the simulation is a set of programming options, selected to preferentially stimulate the nerve in a preselected target volume. After an initial electrode configuration is selected, the configuration may be reprogrammed to optimize its effectiveness, even after the device is implanted in the patient [MANOLA L, Holsheimer J, Veltink P H, Bradley K, Peterson D. Theoretical investigation into longitudinal cathodal field steering in spinal cord stimulation. Neuromodulation (February, 2007):120-132].

The invention also contemplates an electrode configuration in which all electrode contacts connected as anodes may have a different voltage, and all electrode contacts connected as cathodes may have a different voltage. For the electrodes implanted parallel to the vagus nerve, this may occur when the anode and cathode voltages for different electrodes change rapidly in sequence from one end of the device to the other, in an attempt to entrain or inhibit action potentials of certain fibers of the nerve bundle. This may be done, for example, so as to stimulate particular afferent versus efferent fibers. In this example, the temporal sequence of electrode activation by the device may be in the orthodromic or antidromic direction for any particular fiber within the vagus nerve.

FIG. 2 illustrates different electrode assemblies that are contemplated by the invention. The assemblies shown as FIGS. 2A and 2B are adapted from the disclosure of PERRYMAN et al [WO/2012/138782, entitled Implantable lead, to PERRYMAN et al], which describes how the device contains a dipole antenna for the receipt of externally transmitted energy, as well as electronic components for the generation of electrical stimulation pulses through the electrodes. In FIG. 2A, the modulating device 300 comprises four electrodes 340 that are separated and surrounded by electrically insulating material 205. As shown, the device has the style of a paddle, so that the stimulation occurs preferentially on the side of the paddle with exposed electrodes 340. The device has attached extension tubing 201 with a central lumen 204 that is intended for the introduction of a stylet or other tool used during implantation of the device 300. In FIG. 2B, the modulating device 300 comprises eight electrodes 340 that are separated by electrically insulating material 205. The device also has attached extension tubing 201 with a central lumen 204. As shown, the device in FIG. 2B has the style of a cylinder, so that stimulation from the exposed electrodes 340 occurs symmetrically with respect to the axis of the cylinder.

Unlike the disclosure by PERRYMAN et al, the present invention contemplates removal of the extension tubing 201 after implantation of the device 300. This may be performed by introducing a cutting tool into the lumen 204 of the tubing 201, then cutting through the tubing along its perimeter to separate the tubing from the device 300. The tubing is then withdrawn slightly to permit anchoring of the device 300, e.g., by injection of surgical glue through the lumen 204 about the tail of device 300. Then, the tubing 201 is completely withdrawn from the patient, leaving the device 300 at its implantation site. However, preferred methods for separating the device 300 from the tubing 201 are illustrated in connection with FIG. 2C, and other methods for anchoring the device to surrounding tissue are disclosed below.

The length of device 300 (without tubing) must be sufficient to accommodate the number of electrodes 340 that it houses. The device length is also generally proportional to the length of its dipole antenna that is used to receive the electromagnetic energy that powers the device, with the understanding that although the dipole antenna is preferably straight, it may also be to some extent twisting or meandering. The length of the antenna in turn determines the preferred frequency of received electromagnetic energy. For example, for an 8.2 cm antenna, the preferred frequency may be 868 MHz, and for a 4 cm antenna, the preferred frequency may be 1.775 GHz. For use of frequencies in the unlicensed ISM/SRD bands of 2.400 to 2.4835 GHz, the preferred antenna length may be 2.85 to 2.95 cm. Thus, as the number of electrodes housed by the device decreases, the antenna length will generally decrease, resulting in the need to use higher frequency electromagnetic waves to power the device.

FIG. 2C illustrates an exemplary electrode assembly 340 on the device 300 according to a preferred embodiment of the present invention. The device contains two electrodes in a cylindrical-style stimulator. As shown, electrode assembly 340 includes an active electrode 502 and a return electrode 504 coupled to the pulse generating circuits of the device 300. Active and return electrodes 502 and 504, respectively, are spaced a suitable distance to allow for the formation of an electromagnetic field around electrode assembly 340 for modulation of nerve(s) at the target region (not shown). In this embodiment, electrodes 502 and 504 are spaced from each other with insulating material 205 by about 5-50 mm, preferably between about 10-20 mm. As shown, the electrodes are exposed along only part of the diameter of the cylinder, so as to be able to direct the formed electromagnetic field pulses in a particular direction, namely, towards the nerve that they are intended to stimulate.

Although there are a number of sizes and shapes that would suffice to implement electrodes 502 and 504, by way of example, electrodes may be between about 1.0-1.5 mm long (such as 1.2 mm), may have an outside diameter of between about 2.6-2.85 mm (such as 2.7 mm), and may have an inside diameter of between about 2.5-2.75 mm (such as 2.7 mm). A suitable electrode may be formed from Pt-IR (90%/10%), although other materials or combinations or materials may be used, such as platinum, tungsten, gold, copper, palladium, silver.

Those skilled in the art will also recognize that a variety of different shapes and sizes of electrodes may be used. By way of example only, electrode shapes according to various aspects of the present invention can include ball shapes, twizzle shapes, spring shapes, twisted metal shapes, annular shapes, solid tube shapes, flat shapes or the like. Alternatively, the electrode(s) may comprise a plurality of filaments, rigid or flexible brush electrode(s), coiled electrode(s) or the like. Alternatively, the electrode may be formed by the use of formed wire (e.g., by drawing round wire through a shaping die) to form electrodes with a variety of cross-sectional shapes, such as square, rectangular, L or V shaped, or the like.

The device shown in FIG. 2C differs from the devices shown in FIGS. 2A and 2B in that it contains a connecting piece 210 that is interposed between the part of the device 300 containing the electrodes 340 and the tubing 201. The purpose of the connecting piece 210 is to make it easy to disconnect the tubing from the stimulator device 300 once the device is finally implanted. The connecting piece 210 shown in FIG. 2D contains a male part 211 and a female part 212 that interconnect with one another when the tubing 201 is being used to position the device 300. The male part is permanently connected to the tubing, and the female part is connected permanently to the device 300. The parts are held together with thread or wire 213 that is threaded through aligned holes in the insert 215 of the male part 211 and walls of the groove 216 of the female part 212. As shown in FIG. 2E, when the thread is pulled out, the interconnecting male part 211 disconnects from the female part 212 when the tubing 201 is pulled.

An alternate connecting piece 210 is shown in FIG. 2F. In that case, a male part 218 and a female part 219 interconnect with one another when the tubing 201 is being used to position the device 300. The male part is permanently connected to the tubing 201, and the female part is connected permanently to the device 300. The pieces are mated through an insert 215 in the male part 218 that is situated in a groove 216 of the female part 219. In this case, the pieces are held together magnetically, rather than by a thread through aligned holes. As shown, the male part 218 is an electromagnet that is powered when the tubing 201 is being used to position the stimulator 300. The electromagnet comprises a coil wound around a core of ferromagnetic material such as soft iron. The magnetic field that the electromagnet produces holds the female part 219 to the male part 218, because the female part is either a permanent magnet or is made of soft-magnetic material, i.e., it becomes magnetic in the presence of the magnetic field produced by the electromagnet (e.g., a piece of iron). When current through windings of the electromagnet is turned off, the male and female pieces will separate when the tubing 201 is pulled.

An advantage of using the connecting piece 210 shown in FIG. 2F is that it allows the device 300 to be re-positioned magnetically after the tubing 201 and its attached male part 218 have been removed. This is because a magnetic field applied externally to the patient may be used to manipulate the location and orientation of the female part 219 in FIG. 2F (and therefore the stimulator 300 to which the female part 219 is permanently attached), whether the female part is a permanent magnet or is made of soft-magnetic material [GILLIES, G. T., Ritter, R. C., Broaddus, W. C., Grady, M. S., Howard, M. A., and McNeil, R. G. Magnetic manipulation instrumentation for medical physics research. Review of Scientific Instruments 65(March, 1994):533-562; Jake J. ABBOTT, Olgac Ergeneman, Michael P. Kummer, Ann M. Hirt, and Bradley J. Nelson. Modeling magnetic torque and force for controlled manipulation of soft-magnetic bodies. IEEE Transactions on Robotics 23(June, 2007)1247-1252].

The requirements for device re-positioning would be based upon images of the device 300 in its originally implanted site and orientation, as compared with images of the device in its present, presumably non-ideal, site or orientation. Such imaging may involve different potential imaging modalities, such as fluoroscopy or MRI. The preferred imaging methods involve ultrasound, as described below in connection with the use of ultrasound imaging to implant the stimulator device. In order to explain the invention's methods for imaging and implanting the device 300 into the neck of the patient, it is first necessary to summarize the relevant anatomy of the neck, as follows.

FIG. 3A illustrates some of the major structures of the neck. As shown, the common carotid artery 100 extends from the base of the skull 102 through the neck 104 to the first rib and sternum (not shown). Carotid artery 100 includes an external carotid artery 106 and an internal carotid artery 108 and is protected by fibrous connective tissue called the carotid sheath. The carotid sheath is located at the lateral boundary of the retopharyngeal space at the level of the oropharynx on each side of the neck 104 and deep to the sternocleidomastoid muscle. The three major structures within the carotid sheath are the common carotid artery 100, the internal jugular vein 110 and the vagus nerve (not shown). The carotid artery lies medial to the internal jugular vein and in most patients, the vagus nerve is situated posteriorly between the two vessels.

FIG. 3A also illustrates the approximate locations of the cervical vertebrae C1 through C7. The thyroid cartilage, the largest of the cartilages that make up the cartilage structure in and around the trachea that contains the larynx, lies at the vertebral levels of C4 and C5. The laryngeal prominence 111 (Adam's apple) in the middle of the neck is formed by the thyroid cartilage at approximately vertebral level C4. Inferiorly, the ring of the cricoid cartilage (the only complete ring of cartilage around the trachea) may be palpated at vertebral level C6. A flexion-extension palpation method may be used to identify vertebral level C7 [Seokyung SHIN, Duck-Mi Yoon, and Kyung Bong Yoon. Identification of the correct cervical level by palpation of spinous processes. Anesth Analg 112(2011):1232-1235].

As indicated above, the vagus nerve is situated within the carotid sheath, near the carotid artery and the interior jugular vein. The left vagus nerve is sometimes selected for stimulation because stimulation of the right vagus nerve may produce undesired effects on the heart, but depending on the application, the right vagus nerve or both right and left vagus nerves may be stimulated instead. Typically, the location of the carotid sheath or interior jugular vein in a patient (and therefore the location of the vagus nerve) will be ascertained preliminarily by feel and eventually by ultrasound imaging. Proceeding from the skin and fat of the neck to the vagus nerve, the shortest line may pass successively through the platysma muscle 82, the sternocleidomastoid muscle 65, and the carotid sheath (see FIGS. 3B and 3C). If such direct access to the vagus nerve is desired, it may be attempted at about the level of cervical vertebra C5 to C6, although direct access to the vagus nerve through the sternocleidomastoid muscle 65 might also be attempted anywhere between the middle of vertebra C4 and the middle of vertebra C7. Access at more cephalad vertebrae levels is ordinarily avoided because the carotid sheath there also contains nerve branches of the ansa cervicalis, which is part of the cervical plexus located from the C1 to C4 cervical segment in the neck. A less direct route to the carotid sheath (and vagus nerve) may be along a line that passes just outside the edge of the sternocleidomastoid muscle 65 at the boundary of the posterior or anterior triangles (FIG. 3C).

Figure 4A:
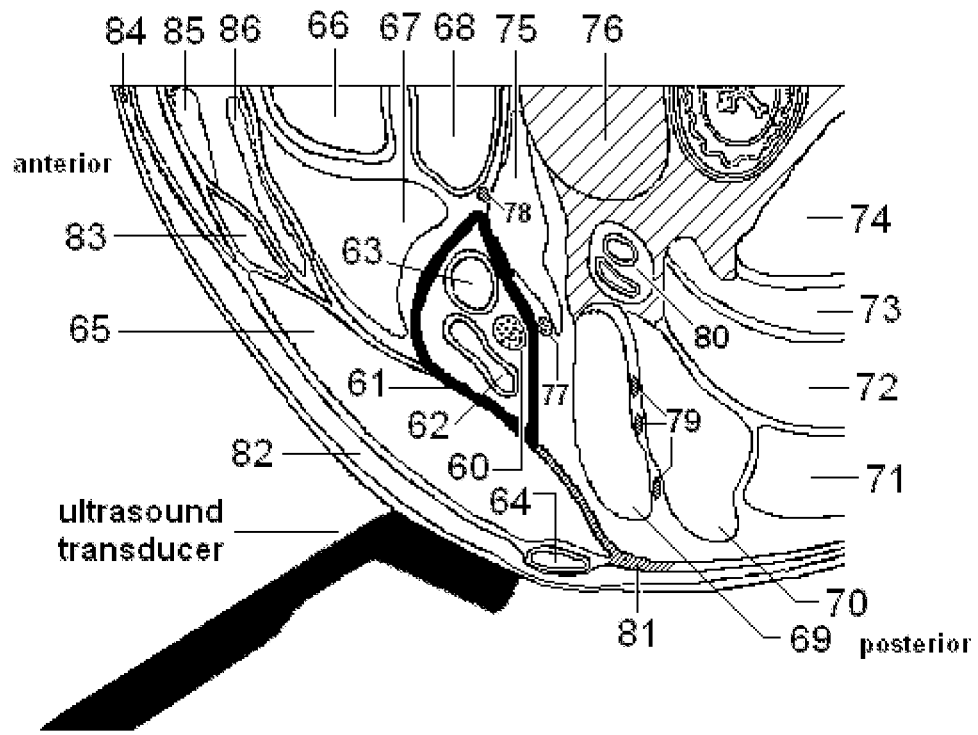
FIG. 4 illustrates the positioning of an ultrasound imaging transducer that is used to image a vagus nerve in the patient's neck, wherein the transducer is applied to the surface of the neck in the vicinity of the identified anatomical structures (FIG. 4A), the structural arrangement of which may to vary from individual to individual as indicated by the percentages shown in FIG. 4B.

FIG. 4A provides a more detailed cross-sectional view of the patient's neck, which may be viewed using an ultrasound transducer/probe placed at approximately the indicated location at the level of vertebra C6. The preferred ultrasound transducer/probe style is shown to be the "hockey-stick" style, so-called because of its compact and unobtrusive shape, which is commercially available from most ultrasound machine manufacturers. By way of example, the Hitachi Aloka UST-536 19 mm Hockey Stick style Transducer for superficial viewing has a frequency range of 6-13 MHz, a scan angle of 90 degrees, and a scan width of 19 mm (Hitachi Aloka Medical America, 10 Fairfield Boulevard, Wallingford Conn. 06492).

The vagus nerve 60 is identified in FIG. 4A, along with the carotid sheath 61 that is identified there in bold peripheral outline. The carotid sheath encloses not only the vagus nerve, but also the internal jugular vein 62 and the common carotid artery 63. Structures that may be identified near the surface of the neck include the external jugular vein 64 and the sternocleidomastoid muscle 65 (see also FIG. 6, in which the sternocleidomastoid muscle protrudes when the patient turns his head). Additional organs in the vicinity of the vagus nerve include the trachea 66, thyroid gland 67, esophagus 68, scalenus anterior muscle 69, scalenus medius muscle 70, levator scapulae muscle 71, splenius colli muscle 72, semispinalis capitis muscle 73, semispinalis colli muscle 74, longus colli muscle and longus capitis muscle 75. The sixth cervical vertebra 76 is shown with bony structure indicated by hatching marks. Additional structures shown in the figure are the phrenic nerve 77, sympathetic ganglion 78, brachial plexus 79, vertebral artery and vein 80, prevertebral fascia 81, platysma muscle 82, omohyoid muscle 83, anterior jugular vein 84, sternohyoid muscle 85, and sternothyroid muscle 86.

The anatomy shown in FIG. 4A may be regarded as typical, but it should be understood that the implantation of the stimulator device must take into account the anatomical variability that is observed from individual to individual. In approximately 5 percent of individuals, the vagus nerve has an unusual anatomical course that is possibly associated with abnormal thyroid gland anatomy. Also, the vagus nerve of approximately 25% of individuals has an atypical position within the carotid sheath [GIBSON A. Bilateral abnormal relationship of the vagus nerve in its cervical portion. J Anat Physiol 49(1915):389-392; TUBBS R S, Loukas M, Shoja M M, Blevins D, Humphrey R, Chua G D, Kelly D R, Oakes W J. An unreported variation of the cervical vagus nerve: anatomical and histological observations. Folia Morphol (Warsz) 66(February, 2007):155-157; PARK J K, Jeong S Y, Lee J H, Lim G C, Chang J W. Variations in the course of the cervical vagus nerve on thyroid ultrasonography. AJNR Am J Neuroradiol 32(July, 2011):1178-1181; DIONIGI G, Chiang F Y, Rausei S, Wu C W, Boni L, Lee K W, Rovera F, Cantone G, Bacuzzi A. Surgical anatomy and neurophysiology of the vagus nerve (VN) for standardised intraoperative neuromonitoring (IONM) of the inferior laryngeal nerve (ILN) during thyroidectomy. Langenbecks Arch Surg 395(July, 2010):893-899; BROWN H, Hidden G, Ledroux M, Poitevan L. Anatomy and blood supply of the lower four cranial and cervical nerves: relevance to surgical neck dissection. Proc Soc Exp Biol Med 223(April, 2000):352-361].

Figure 4B:
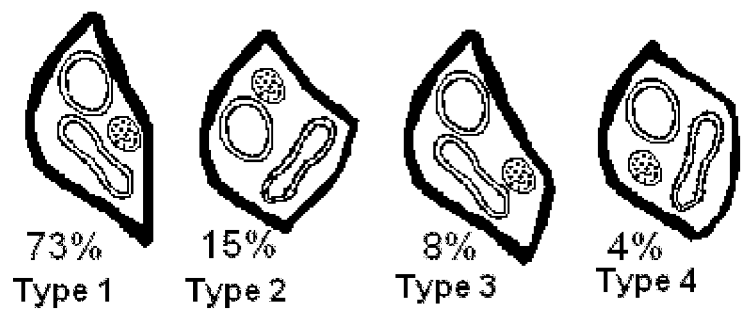

Anatomical variation within the carotid sheath, as reported by DIONIGI et al, is illustrated in FIG. 4B, along with the approximate percentage of individuals having that anatomy. In approximately 73% of individuals, the location of the vagus nerve is as shown in FIG. 4A, in which the nerve is in a posterior location within the carotid sheath between the common carotid artery and internal jugular vein (Type 1). In approximately 15% of individuals, the nerve is in a posterior location but is closely associated with the common carotid artery (Type 2). In approximately 8% of individuals, the nerve is in a posterior location but is closely associated with the internal jugular vein (Type 3). And in approximately 4% of individuals, the nerve is in an anterior location within the carotid sheath between the common carotid artery and internal jugular vein (Type 4). The apparent reason for the existence of such anatomical variability is that the fetal vagus nerve migrates within the carotid sheath, and this migration may be incomplete or unusual in some individuals [MIYAKE N, Hayashi S, Kawase T, Cho B H, Murakami G, Fujimiya M, Kitano H. Fetal anatomy of the human carotid sheath and structures in and around it. Anat Rec (Hoboken) 293(March, 2010):438-445].

The conventional method for locating a cervical vagus nerve involves the palpation of anatomical landmarks such as muscles, bones, cartilage and blood vessels by the treatment provider. This method is inexact because of individual variations in patient anatomy, which should be considered in devising the anatomical path along which implantation of the stimulator in the vicinity of the vagus nerve is performed. Preferably, the location of a vagus nerve is determined by imaging with an ultrasound probe as shown in FIG. 4A [KNAPPERTZ V A, Tegeler C H, Hardin S J, McKinney W M. Vagus nerve imaging with ultrasound: anatomic and in vivo validation. Otolaryngol Head Neck Surg 118(January, 1998):82-85; GIOVAGNORIO F and Martinoli C. Sonography of the cervical vagus nerve: normal appearance and abnormal findings. AJR Am J Roentgenol 176(March, 2001): 745-749]. On transverse scans, the vagus nerve has a honeycomb appearance with 2 to 4 hypoechoic rounded fascicles surrounded by a hyperechoic epineurium. In addition to an unusual anatomical course of the vagus nerve, the ultrasound imaging may also reveal potential problems such as inflammation of the nerve that may contraindicate the use of vagus nerve stimulation [Einar P V WILDER-SMITH. Nerve Ultrasound: Ready for clinical practice? Neurology Asia 17(January, 2012):1-4].

To the extent that there is variation in the distance between the skin and vagus nerve as a function of position up and down the neck, the stimulator is preferably implanted in such a way that the distance is minimized. Accordingly, in a preferred embodiment of the invention, the vagus nerve is imaged as shown in FIG. 4A, continuously from the vertebra levels C4 to C7, so as to construct a three-dimensional image of the carotid sheath within the neck, along with surrounding tissue. This is accomplished by attaching the ultrasound transducer to a computer-controlled positioning device that moves the transducer down the neck, storing images of the ultrasound images along the way. This computer-controlled device will also be used for the robotic insertion of a needle into the neck, as described below in connection with FIG. 9.

The ultrasound imaging will also be used to identify and locate structures lying near the vagus nerve, or along the implantation path, that may be either potentially damaged during implantation of the electrode or unintentionally electrically stimulated along with the vagus nerve [Barys IHNATSENKA and André P Boezaart. Applied sonoanatomy of the posterior triangle of the neck. Int J Shoulder Surg 4(March, 2010): 63-74]. These include blood vessels, cervical sympathetic ganglia, and the phrenic nerve. Large blood vessels such as the common carotid artery or internal jugular vein are most easily identified by using color flow Doppler ultrasound imaging. We note too that the internal jugular vein is collapsible with slight pressure of the ultrasound probe. Smaller vessels that may be damaged by the implantation procedure may also be identified with the aid of gas-filled microbubbles as a contrast agent, as now described.

The human vagus nerve is supplied by a distinct vagal artery and vein that lie on the anterior aspect of the nerve [FERNANDO D A, Lord R S. The blood supply of vagus nerve in the human: its implication in carotid endarterectomy, thyroidectomy and carotid arch aneurectomy. Ann Anat 176 (April, 1994):333-337]. KNAPPERTZ et al (cited above) were unable to delineate the vagal artery with color flow Doppler ultrasound imaging. However, conventional Doppler-based imaging techniques are unable to detect low velocity blood flow in smaller vessels, the chief difficulty being that blood is a weak reflector of ultrasound. One method to overcome this difficulty is to inject brighter ultrasound reflectors than blood into the vascular system. Gas filled microbubbles are one such reflector or contrast agent [Matthew BRUCE, Mike Averkiou, and Jeff Powers. Ultrasound contrast in general imaging research. (2007). Philips Medical Systems, Global Information Center, P.O. Box 1286, 5602 BG Eindhoven, The Netherlands, pp. 1-19].

Note that this microbubble method may be useful not only for identifying the course and density of vagus nerve blood vessels, but also for testing the operation of the electrical stimulator and determining whether the vagus nerve has been damaged, for the following reason. When the vagus nerve is electrically stimulated, its metabolic needs increase, such that there is reflex-increased blood flow within the vagal artery and its associated arterioles. Thus, one test for whether the vagus nerve is being stimulated is to measure blood flow in the vagal artery and compare it with the flow when the vagus nerve is not being stimulated. Therefore, according to the present invention, one method for demonstrating stimulation of a vagus nerve is to measure a change in vagal artery blood flow, preferably using ultrasound contrast agents.

In some species such as the pig, the cervical sympathetic chain lies within the carotid sheath alongside the vagus nerve [DING P, Tufano R P, Campbell-Malone R, Feng W, Kim S J, German R Z. Horner syndrome after carotid sheath surgery in a pig: anatomic study of cervical sympathetic chain. Comp Med 61(May, 2011):453-456]. In humans, the cervical sympathetic chain, which may be imaged using an ultrasound transducer, lies outside the carotid sheath. Nevertheless, in some individuals, it may lie quite close to the sheath [Philip W H PENG and Samer Narouze. Sonoanatomy of the Cervical Sympathetic Chain. Chapter 3 (pp 31-44) In: Samer Nabil Narouze. Ultrasound Guidance for Interventional Pain Management of Cervical Pain Syndromes An anatomical and clinical study. Dissertation at the Universiteit Maastricht. Minderbroedersberg 4-6, 6211 LK Maastricht, The Netherlands (2012)]. Therefore, in such individuals, care must be taken to avoid damaging or electrically stimulating the sympathetic chain, such as the middle cervical ganglion (78 in FIG. 4A). Otherwise, the patient may develop Horner syndrome, with symptoms affecting the eye and face.

The phrenic nerve in humans may also lie close to a vagus nerve (77 in FIG. 4A), although the distance may again vary from individual to individual. The likelihood of electrical co-stimulation of the vagus and phrenic nerves is sufficiently great that it has been the subject of a patent application that seeks to minimize the co-stimulation effects. Thus, in patent application JP2008/081479A, entitled Vagus nerve stimulation system, to YOSHIHOTO, a system is described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve. It discloses electrical stimulation during particular phases of the respiratory cycle, for the following reason. Because the vagus nerve is near the phrenic nerve, Yoshihoto indicates that the phrenic nerve will sometimes be electrically stimulated along with the vagus nerve. The phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual.

If the vagus and phrenic nerves in an individual are sufficiently close to one another to be electrically co-stimulated, there is also the possibility that the phrenic nerve may be damaged during the implantation of a vagus nerve stimulator. However, such damage may be avoided if the location of the phrenic nerve is first imaged using the ultrasound probe. According to KESSLER et al, the location of the phrenic nerves is a function of the vertebral level. They found that the phrenic nerve and brachial plexus (79 in FIG. 4A) are within 2 mm of each other at the cricoid cartilage level, with additional 3 mm separation for every cm more caudal in the neck. However, this too may vary from individual to individual [KESSLER J, Schafhalter-Zoppoth I, Gray A T. An ultrasound study of the phrenic nerve in the posterior cervical triangle: implications for the interscalene brachial plexus block. Reg Anesth Pain Med 33(June, 2008):545-550]. Other nerves that could be potentially damaged in some individuals, because of their proximity to the carotid sheath, and because they are possibly in the path of implantation, are the spinal accessory nerve and superior cardiac nerve [Ong Cheng KANG and Chong Vincent Fook Hin. The glossopharyngeal, vagus and spinal accessory nerves. European Journal of Radiology 74 (2010) 359-367].

One preferably implants the vagus nerve stimulator in such a way as to be as distant as possible from other nerves, also orienting the stimulator's electrodes (e.g., 502 and 504 in FIG. 2C) towards the vagus nerve and away from other nerves. Nevertheless, depending on the individual patient, some co-stimulation of other nerves may be unavoidable. Even within a vagus nerve, one prefers to stimulate particular fiber types and avoid stimulation of other fiber types, and this selectivity cannot be achieved simply by adjustment of the position of the stimulator. In the case of vagal fiber selectivity, preferential nerve fiber stimulation is accomplished by selection of the stimulus waveform, and the same type of waveform-selective stimulation may be used to preferentially activate only the vagus nerve, as now described. Selectivity that is achieved through physical placement of the stimulator will be described later, in connection with the methods that are used to implant the stimulator.

A waveform may be designed to selectively stimulate only one of two nerves whether the nerves lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. Waveform selection methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295]. Parameters for the nerve stimulation include power level, frequency and train duration (or pulse number). The stimulation characteristics of each pulse, such as depth of penetration, strength and selectivity, depend on the rise time and peak electrical energy transferred to the electrodes, as well as the spatial distribution of the electric field that is produced by the electrodes. The rise time and peak energy are governed by the electrical characteristics of the stimulator and electrodes, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurto, Przemystaw Ptonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Pulses may be monophasic, biphasic or polyphasic. Embodiments of the invention include those that are fixed frequency, where each pulse in a train has the same inter-stimulus interval, and those that have modulated frequency, where the intervals between each pulse in a train can be varied.

Figure 5A:
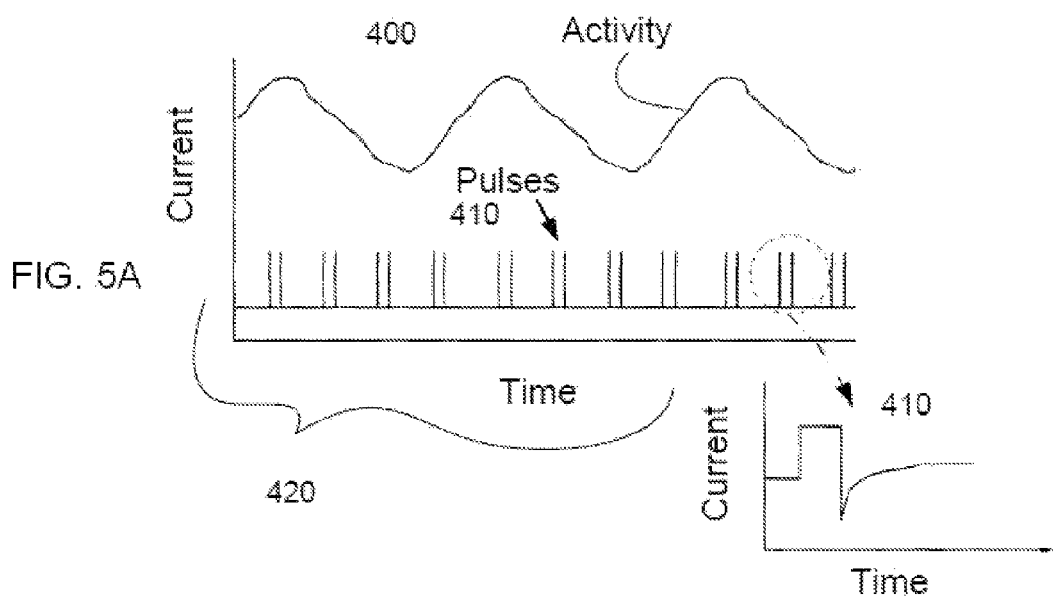
FIG. 5 illustrates an exemplary electrical voltage/current profile for a blocking and/or modulating impulse applied to a portion or portions of a nerve in accordance with an embodiment of the present invention (FIG. 5A), wherein the impulses may appear in a pattern of bursts (FIGS. 5B and 5C).

FIG. 5A illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are produced within the patient by the electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the electrodes 340 that deliver the stimulating, blocking and/or modulating impulse 410 to the nerve. The parameters of the modulation signal 400, such as the frequency, amplitude, duty cycle, pulse width, pulse shape, etc., are preferably programmable. An external communication device may modify the pulse generator programming to improve treatment (380 in FIG. 1A).

In addition, techniques according to the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the tissue being treated, as well as the outputs of various sensors which sense prevailing conditions prevailing in this tissue, whereby the user of the system can manually adjust the signal, or have it automatically adjusted by feedback, to provide an electrical stimulation signal of whatever type the user wishes, who can then observe the effect of this signal on a tissue being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, square, triangular or trapezoidal waves are preferred waveforms for stimulation. The electrical impulse will typically have a frequency of between about 1-500 Hz, preferably about 1 to 50 Hz, and more preferably about 10-35 Hz. In an exemplary embodiment, the frequency for the impulse received by the nerve is about 25 Hz. The preferred fixed voltage received by the nerve is between about 1-20 V and will typically vary depending on the size and type of electrode and the distance between the electrode and the nerve. In certain embodiments where the nerve is directly attached to the nerve (or implanted adjacent to the nerve), the fixed voltage is preferably about 1 to 4 volts, more preferably about 2 volts. In other embodiments, wherein the electrode is, for example, injected into the patient and implanted outside of the sheath, the voltage is preferably between about 7-15 volts and more preferably about 10 V. In embodiments wherein the current is fixed or held constant, the preferred fixed current is about 0.5 mA to about 20 mA. Similar to voltage, the fixed current will vary depending on the size and type of electrode and its distance from the nerve. In those embodiments where the electrode is adjacent to, or on, the nerve, the current is preferably about 0.5 to 5 mA and more preferably about 3.5 mA. In those embodiments, where the electrode is spaced from the nerve (just as an injectable electrode outside of the sheath), the current is preferably about 7-15 mA and more preferably about 10 mA. The modulation signal may have a pulse width selected to influence the therapeutic result, such as about 1 microsecond to about 1000 microseconds, preferably about 200 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz.

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Figure 5B:
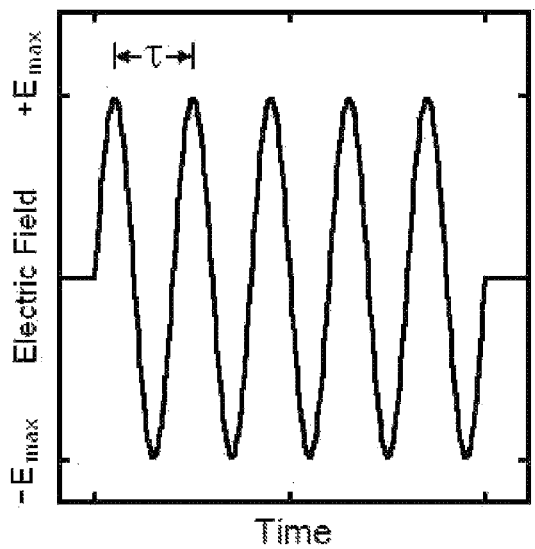
Figure 5C:
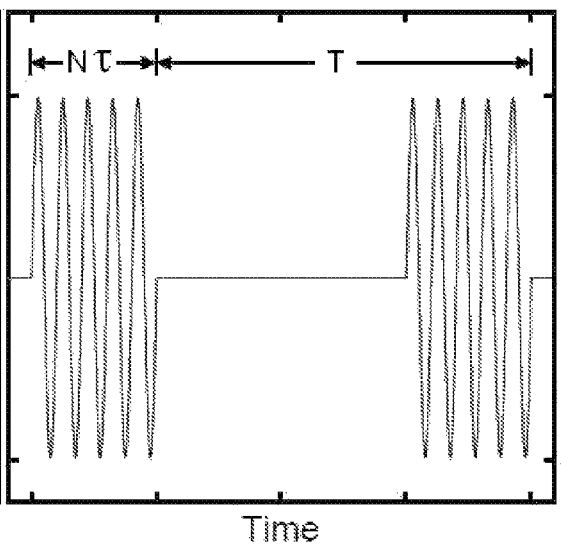

In other embodiments, bursts of sinusoidal pulses are used as a stimulation waveform, as shown in FIGS. 5B and 5C. As seen there, individual sinusoidal pulses have a period of □, and a burst consists of N such pulses. This is followed by a period with no signal (the inter-burst period). The pattern of a burst followed by silent inter-burst period repeats itself with a period of T. For example, the sinusoidal period □ may be 200 microseconds; the number of pulses per burst may be N=5; and the whole pattern of burst followed by silent inter-burst period may have a period of T=40000 microseconds, which is comparable to 25 Hz stimulation (a much smaller value of T is shown in FIG. 5C to make the bursts discernable). When these exemplary values are used for T and □, the waveform contains significant Fourier components at higher frequencies (1/200 microseconds=5000/sec), as compared with those contained in nerve stimulation waveforms, as currently practiced.

Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters □, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation: The Early Experiments. Physical Therapy 82 (October, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (October, 2008): 1167-1176; Alex R WARD. Electrical Stimulation Using Kilohertz-Frequency Alternating Current. Physical Therapy 89 (February, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (February, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 5B and 5C may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [Patent application US20120197369, entitled Selective high frequency spinal cord modulation for inhibiting pain with reduced side effects and associated systems and methods, to ALATARIS et al.; Adrian A L KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, Md., Mar. 24-27, 2011].

Those methods involve high-frequency modulation in the range of from about 1.5 KHz to about 50 KHz, which is applied to the patient's spinal cord region. However, such methods are different from the present invention because, for example, they do not involve a bursting waveform, as in the present invention; they necessarily involve A-delta and C nerve fibers and the pain that those fibers produce, whereas the present invention does not; they may involve a conduction block applied at the dorsal root level, whereas the present invention may stimulate action potentials without blocking of such action potentials; and/or they involve an increased ability of high frequency modulation to penetrate through the cerebral spinal fluid, which is not relevant to the present invention. In fact, a likely explanation for the reduced back pain that is produced by their use of frequencies from 10 to 50 KHz is that the applied electrical stimulus at those frequencies causes permanent damage to the pain-causing nerves, whereas the present invention involves only reversible effects [LEE R C, Zhang D, Hannig J. Biophysical injury mechanisms in electrical shock trauma. Annu Rev Biomed Eng 2(2000):477-509].

However, the threshold for activation of fiber types also depends on the amplitude and/or duration of the stimulation, and for a given stimulation frequency, the threshold increases as the fiber size decreases. The threshold for generating an action potential in nerve fibers that are impaled with electrodes is traditionally described by Lapicque or Weiss equations, which describe how together the width and amplitude of stimulus pulses determine the threshold, along with parameters that characterize the fiber (the chronaxy and rheobase). For nerve fibers that are stimulated by electric fields that are applied externally to the fiber, as is the case here, characterizing the threshold as a function of pulse amplitude and frequency is more complicated, which ordinarily involves the numerical solution of model differential equations or a case-by-case experimental evaluation [David BOINAGROV, Jim Loudin and Daniel Palanker. Strength-Duration Relationship for Extracellular Neural Stimulation: Numerical and Analytical Models. J Neurophysiol 104(2010):2236-2248].

For example, REILLY describes a model (the spatially extended nonlinear nodal model or SENN model) that may be used to calculate minimum stimulus thresholds for nerve fibers having different diameters [J. Patrick REILLY. Electrical models for neural excitation studies. Johns Hopkins APL Technical Digest 9(January, 1988): 44-59]. According to REILLY's analysis, the minimum threshold for excitation of myelinated A fibers is 6.2 V/m for a 20 □m diameter fiber, 12.3 V/m for a 10 □m fiber, and 24.6 V/m for a 5 □m diameter fiber, assuming a pulse width that is within the contemplated range of the present invention (1 ms). It is understood that these thresholds may differ slightly from those produced by the waveform of the present invention as illustrated by REILLY's figures, for example, because the present invention prefers to use sinusoidal rather than square pulses. Thresholds for B and C fibers are respectively 2 to 3 and 10 to 100 times greater than those for A fibers [Mark A. CASTORO, Paul B. Yoo, Juan G. Hincapie, Jason J. Hamann, Stephen B. Ruble, Patrick D. Wolf, Warren M. Grill. Excitation properties of the right cervical vagus nerve in adult dogs. Experimental Neurology 227 (2011): 62-68]. If we assume an average A fiber threshold of 15 V/m, then B fibers would have thresholds of 30 to 45 V/m and C fibers would have thresholds of 150 to 1500 V/m. The present invention produces electric fields at the vagus nerve in the range of about 6 to 100 V/m, which is therefore generally sufficient to excite all myelinated A and B fibers, but not the unmyelinated C fibers. In contrast, invasive vagus nerve stimulators that have been used for the treatment of epilepsy have been reported to excite C fibers in some patients [EVANS M S, Verma-Ahuja S, Naritoku D K, Espinosa J A. Intraoperative human vagus nerve compound action potentials. Acta Neurol Scand 110(2004): 232-238].

It is understood that although devices of the present invention may stimulate A and B nerve fibers, in practice they may also be used so as not to stimulate the large A fibers (A-delta) and B fibers. In particular, if the stimulator amplitude has been increased to the point at which unwanted side effects begin to occur, the operator of the device may simply reduce the amplitude to avoid those effects. For example, vagal efferent fibers responsible for bronchoconstriction have been observed to have conduction velocities in the range of those of B fibers. In those experiments, bronchoconstriction was only produced when B fibers were activated, and became maximal before C fibers had been recruited [R. M. McALLEN and K. M. Spyer. Two types of vagal preganglionic motoneurones projecting to the heart and lungs. J. Physiol. 282(1978): 353-364]. Because proper stimulation with the disclosed devices does not result in the side-effect of bronchoconstriction, evidently the bronchoconstrictive B-fibers are possibly not being activated when the amplitude is properly set. Also, the absence of bradycardia or prolongation of PR interval suggests that cardiac efferent B-fibers are not stimulated. Similarly, A-delta afferents may behave physiologically like C fibers. Because stimulation with the disclosed devices does not produce nociceptive effects that would be produced by jugular A-delta fibers or C fibers, evidently the A-delta fibers may not be stimulated when the amplitude is properly set.

For acute treatments, the nerve stimulation may be administered for a predetermined duration, such as between about 5 minutes and about 1 hour, or between about 5 minutes and about 24 hours. For other treatments, the nerve stimulation may be administered as the need arises, or on an intermittent schedule over a period of days or weeks. A more complete description of the protocols for administering the vagus nerve therapy for particular conditions is found in commonly assigned, co-pending applications that are listed in the section Cross Reference to Related Applications of this application, which are incorporated by reference.

The implantation of conventional vagus nerve stimulators using spiral electrodes is ordinarily performed in open neck surgery, with the patient under general anesthesia[Arun Paul AMAR, Michael L. Levy, Charles Y. Liu and Michael L. J. Apuzzo. Chapter 50. Vagus nerve stimulation. pp. 625-638, particularly 634-635. In: Elliot S. Krames, P. Hunber Peckham, Ali R. Rezai, eds. Neuromodulation. London: Academic Press, 2009; KIRSE D J, Werle A H, Murphy J V, Eyen T P, Bruegger D E, Hornig G W, Torkelson R D. Vagus nerve stimulator implantation in children. Arch Otolaryngol Head Neck Surg 128(November, 2002):1263-1268]. For implantation of stimulator devices of the types illustrated in FIG. 2, however, the patient could be anesthetized only locally in the neck. We note that even the implantation of vagus nerve stimulators in open surgery, as well as carotid endartectomy and thyroid surgery, which are neck surgeries that are considerably more invasive than what is described here, are sometimes also performed using only local anesthesia. Those local anesthesia methods may also be used in the present invention [BERNARD E J, Passannante A N, Mann B, Lannon S, Vaughn B V. Insertion of vagal nerve stimulator using local and regional anesthesia. Surg Neurol 57(February, 2002):94-98; JR SPARGO and D Thomas. Local anaesthesia for carotid endarterectomy. Continuing Education in Anaesthesia, Critical Care & Pain 4(February, 2004):62-65]. An advantage of performing the stimulator implantation with only local anesthesia is that the patient can cooperate in monitoring the successful electrical stimulation by the device as described below, for example, by making vocal sounds that are affected by electrical stimulation of a branch of the vagus nerve (the recurrent laryngeal nerve) or by damage to the vagus nerve.

Even so, it is understood that a vagus nerve stimulator such as the ones shown in FIG. 2, particularly the one in FIG. 2C after tube detachment, could also be implanted during open neck surgery, in lieu of, or in addition to, the spiral electrode that is ordinarily implanted during conventional vagus nerve stimulation implantation. One can consider implanting more than one such stimulator about the vagus nerve. In one configuration, two or more stimulators surround the nerve at a particular vertebral level, each of which has its active and return electrodes facing the nerve. In another configuration, two or more stimulators may be implanted end-to-end, each with electrodes also facing the nerve, with the objective of increasing the nerve coverage over a greater distance along the nerve. In those cases, the stimulators would be constructed with permanently attached loops at their top and bottom, so that the loops could be used to suture the stimulators to surrounding tissue or about the nerve itself. Alternatively, anchorage of the electrodes to the internal jugular vein, common carotid artery, and/or vagus nerve itself can make use of spring-like stimulator attachments like those disclosed later in connection with FIGS. 7B and 8B. Implantation of such an electrode in addition to the conventional spiral electrode would be done in order to provide redundancy of stimulation, for example, in the event that the conventional electrode system fails. This may be done during the open neck surgery as a contingency, but could also be done percutaneously subsequent to failure of the conventional stimulation system, in lieu of performing another open neck surgery around scar tissue [ONEILL B R, Wilberger J E. Revision of vagal nerve stimulator electrodes through a posterior cervical triangle approach: technical note. Neurosurgery 67(2 Suppl Operative, 2010):457-460]. The conventional spiral electrode could also be used as support for the antenna of stimulators of the type shown in FIG. 2, or the spiral electrode itself can be adapted to serve as the antenna. These methods differ from those disclosed by TOCKMAN et al, for example, in that the present methods make use of an antenna and do not make use of a separate implanted pulse generator [Patent application US20120022617, entitled Minimally invasive lead system for vagus nerve stimlation, to TOCKMAN et al].

FIGS. 6-12 illustrate implantation methods directed to the goal of being able to apply an electrical impulse in or around the carotid sheath of a patient. Once the skin of the patient is cleaned and sterilized for the procedure, the target area of the skin on the neck is anesthetized (e.g., with lidocaine or a similar local anesthesia). In a preferred embodiment, a finder needle may be used to first create a path to the target region in or around the carotid sheath. The finder needle is preferably a small access needle having a size in the range of 18-26 gauge, preferably around 22 gauge. Suitable finder needles for use in one or more embodiments of the present invention may be purchased commercially from Epimed (Epimed International, 13958 Diplomat Drive, Farmers Branch, Tex. 75234).

Typically, the finder needle is inserted through the skin surface and advanced to approach or enter the carotid sheath, with its tip in the vicinity of the vagus nerve that is to be electrically stimulated. If the finder needle has a lumen, the needle may be aspirated to ensure that it has not penetrated a vessel such as the jugular vein or carotid artery, and ultrasound may be used to verify the exact placement of the finder needle.

An excitable tissue cell, such as a nerve fiber, is thought to be significantly less sensitive to a transverse electric field perpendicular to the nerve than a longitudinal electric field parallel to the nerve. Applying a longitudinal field increases the effect of this field on the nerve fiber at given frequencies, amplitudes, pulse durations and power levels, as compared with a transverse field. Thus, in these embodiments, the finder needle is preferably advanced to approach the carotid sheath in parallel, assuming that the stimulator device is configured as shown in FIG. 2C. In other embodiments, the finder needle may be advanced to positions transverse to the long axis of the carotid sheath, as shown in FIG. 1 in the following publication: MINER, J. R., Lewis, L. M., Mosnaim, G. S., Varon, J., Theodoro, D. Hoffman, T. J. Feasibility of percutaneous vagus nerve stimulation for the treatment of acute asthma exacerbations. Acad Emerg Med 2012; 19: 421-429.

Figure 6A:
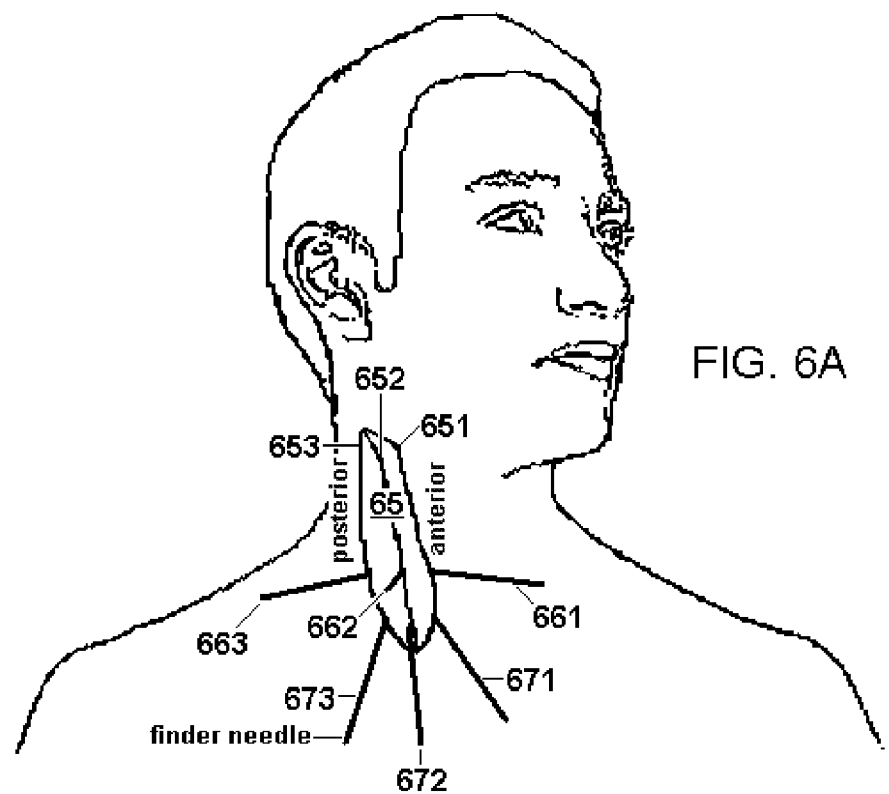
FIG. 6 illustrates different potential locations and directions for the introduction of a finder needle into the neck of patient (FIG. 6A), the selection among which may be made according to the patient's particular anatomy (FIG. 6B).
Figure 6B:
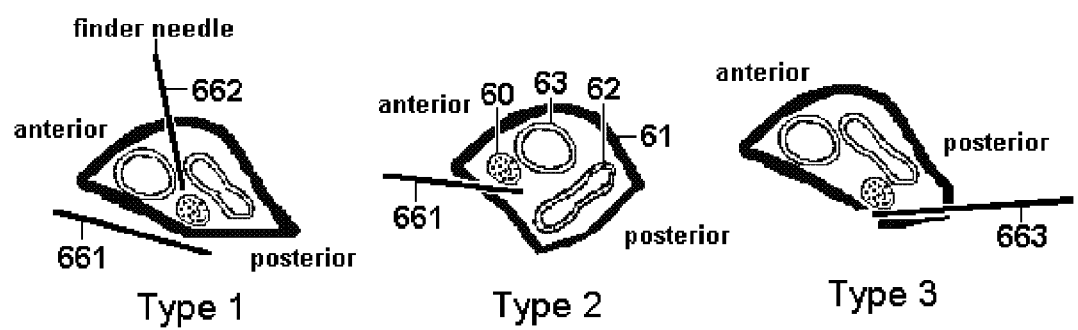

Examples of parallel and transverse finder needle paths to the vagus nerve are illustrated in FIG. 6A. The anterior border 651, central ridge 652, and posterior border 653 of the sternocleidomastoid muscle 65 are indicated in the figure, which may be readily identified from the muscle's bulge when the patient turns his neck far to the side, and which may be subsequently verified by ultrasound imaging. Transverse paths taken by the finder needle to the vagus nerve at the preferred vertebral level may be approached from the anterior border of the muscle 661, from the muscle's central ridge 662, and from the posterior border of the muscle 663. We note that the latter approach is sometimes used in open neck surgery [ONEILL B R, Wilberger J E. Revision of vagal nerve stimulator electrodes through a posterior cervical triangle approach: technical note. Neurosurgery 67(2 Suppl Operative, 2010):457-460]. Note too that the path taken by the finder needle will not necessarily be perfectly straight, as the needle finds a path of least resistance. For example, the transverse path along the posterior border 663 may progress within the prevertebral fascia (81 in FIG. 4A), which is not perfectly straight. Parallel paths taken by the finder needle may be initiated near vertebral level C6 or C7 and then be directed in the direction of the head to reach the vagus nerve at vertebral levels C4 to C6, and these too may be approached from the anterior muscle border 671, from the muscle's central ridge 672, and from the posterior muscle border 673. Additional approaches are also possible, as used in biopsies of the neck, for example, approaches that go through a lobe of the thyroid gland [GUPTA S, Henningsen J A, Wallace M J, Madoff D C, Morello F A Jr, Ahrar K, Murthy R, Hicks M E. Percutaneous biopsy of head and neck lesions with CT guidance: various approaches and relevant anatomic and technical considerations. Radiographics 27(February, 2007):371-390]. Such alternate approaches would generally not be considered if the tubing 201 of the device 300 were not detached and removed, as described in connection with FIG. 2C The preferred path that the finder needle takes in reaching the vagus nerve is based in part upon the anatomy of the patient, which is preliminarily determined using ultrasound imaging. Thus, it is assumed that the location of the vagus nerve within the carotid sheath is known (FIG. 4B), that the location of the phrenic nerve and sympathetic ganglia near the vagus nerve have been determined, and that the location and density of blood vessels, including small vessels, have been determined by color flow Doppler ultrasound in conjunction with microbubbles used as a contrast agent. A path may then be selected as being the most direct route to the vagus nerve, as well as the likelihood that the other structures will not be damaged along the path or stimulated by the implanted stimulator. For example, the decision may be guided by the position of the vagus nerve 60 within the carotid sheath 61, in relation to the internal jugular vein 62 and common carotid artery 63, as illustrated in FIG. 6B. As illustrated there, different transverse paths might be selected. For the Type 1 position of the vagus nerve, the preferred path 662 may be to insert the finder needle through the sternocleidomastoid muscle to a location between the common carotid artery and internal jugular vein until it reaches the vagus nerve. Alternatively, it may be decided that the safest path 661 is an approach from the anterior border of the sternocleidomastoid muscle to a position between the common carotid artery and internal jugular vein but outside the carotid sheath, or a similar approach from the posterior border of the muscle (not shown). In that regard, it is noteworthy that stimulation of the vagus nerve can be accomplished from a location outside the carotid sheath [WU CW, Dionigi G, Chen H C, Chen H Y, Lee K W, Lu I C, Chang P Y, Hsiao P J, Ho K Y, Chiang F Y. Vagal nerve stimulation without dissecting the carotid sheath during intraoperative neuromonitoring of the recurrent laryngeal nerve in thyroid surgery. Head Neck. 2012 Sep. 18. doi: 10.1002/hed.23154, pp. 1-5].

For the Type 2 position of the vagus nerve, the preferred path 661 may be to insert the finder needle from the anterior border of the sternocleidomastoid muscle. For a Type 3 position of the vagus nerve, the preferred path 663 may be to insert the finder needle from the posterior border of the sternocleidomastoid muscle. If the position of the vagus nerve were of Type 4 shown in FIG. 4B, the vagus nerve would already be relatively near the surface of the skin. In that case, one could consider implanting the stimulator along the path shown as 672 in FIG. 6A, to lie within or just outside the carotid sheath. However, one might also simply insert the stimulator immediately under the skin with electrodes directed towards the vagus nerve, without placing the stimulator deep to the sternocleidomastoid muscle. This presumes that the stimulator 300 can generate an electrical signal with sufficient amplitude to modulate the activity of the vagus nerve, considering that as the distance of the vagus nerve from the skin is increased relative to the distance from a point near the carotid sheath, the required amplitude would likewise increase.

If the simulator is like the one shown in FIG. 2C, the path 662 taken by the finder needle for the Type 1 situation in FIG. 6B, between the common carotid artery and internal jugular vein, would not result in the stimulator's electrodes creating an electric field transverse to the vagus nerve. For such a path perpendicular to the vagus nerve, one would instead use a stimulator 300 such as the one shown in FIG. 7 that can bend about a hinge 225 (or use another such flexible stimulator). As described below, after the finder needle has been positioned along a path such as 662 in FIG. 6B, a larger diameter cannula 601 may be introduced adjacent to, or over the finder needle, and if the latter is the case, the finder needle will be withdrawn from the lumen of the cannula 601. The cannula 601 will then accept the introduction of the stimulator 300 within its lumen, which in FIG. 7A is shown in its straight configuration. In addition to the hinge 225, parts of the stimulator 300 include active and return electrodes 502 and 504, a connecting piece 210, and the lumen 204 of tubing 201. The cannula 601 is shown as having a curved distal end, so that as the stimulator is advanced to the end of the cannula, the stimulator is forced into the bent configuration shown in FIG. 7B. In that bent configuration, the electrodes 502 and 504 can then create an electric field that is parallel to the vagus nerve. Thus, with such a stimulator, a parallel electrode configuration can be produced, even if the finder needle is introduced into the patient in a transverse direction.

FIG. 7 also shows optional components that may be used to attach the stimulator 300 to surrounding structures. In the straight configuration shown in FIG. 7A, the device contains ribbon springs 230 that are folded against the tubing 201. After the stimulator assumes the final bent configuration shown in FIG. 7B, the cannula 601 will then be withdrawn so that the ribbon springs 230 are free to assume their unstressed conformations. To prevent them from relaxing to that conformation too quickly as the cannula 601 is withdrawn, threads 234 may be used by the implanter of the device to release the springs slowly. The springs will then be used to hug adjacent tissue, such as the internal jugular vein or common carotid artery, thereby anchoring the stimulator in place. Surgical glue injected through the tubing 201, after detachment connecting piece 210 is separated (see FIG. 2), may also be used to facilitate the anchoring, before the tubing 201 and threads 234 are completely withdrawn.

Such anchoring attachments may also be used with a stimulator that is intended to be implanted along a parallel path (e.g., paths 671, 672, and 673 in FIG. 6A). An example is shown in FIG. 8, in which a coiled spring 240 is initially wound around a stimulator 300 like the one shown in FIG. 2C. The stimulator 300 also comprises active and return electrodes 502 and 504, a lumen 204 of the tubing 201, and a connecting piece 210. As with the electrode shown in FIG. 7, a cannula 601 will accept the introduction of the stimulator 300 of FIG. 8 within its lumen, which in FIG. 8A is shown to be maintaining the coiled spring 240 in its compact, coiled conformation. Once the stimulator 300 reaches its ultimate position near a vagus nerve of the patient, the cannula 601 is withdrawn, and the stimulator may also be rotated about its long axis, so as to release the spring 240. The spring 240 is then free to hug an adjacent structure, such as the vagus nerve itself, thereby anchoring the stimulator within the patient. It is understood that methods for constructing springs of the type shown in FIGS. 7 and 8 are known in the art, wherein the spring may be deployed to exhibit predetermined shape and mechanical properties, although they have not been described in connection with the anchoring of percutaneous peripheral nerve stimulators. Other such deployable attachments may be inflated [e.g., U.S. Pat. No. 3,187,416, entitled Method for manufacturing spiral springs, particularly for watch-making, to TUETEY et al; H PETROSKI. Engineering: Deployable Structures. American Scientist 92(February, 2004):122-126].

To summarize the foregoing disclosure concerning the selection of the anatomical path to be taken by the finder needle—the path selection includes consideration of the length of the stimulator and the number of its electrodes, whether the stimulator's electrodes should produce an electric field that is intended to have particular directionality, whether deployable anchoring attachments will be used to secure the stimulator to particular surrounding tissue, as well as consideration of the electrical waveforms that may be used to preferentially stimulate the vagus nerve and particular fibers within it, the most direct route to the vagus nerve, the likelihood that the other structures will not be damaged or eventually co-stimulated along the path, and the ease with which the finder needle may penetrate and actually follow the intended path. The selection will preferably be made after a thorough ultrasound examination of the patient's neck anatomy, even more preferably by constructing a three-dimensional image that is available as data within a computer.

Introduction of the finder needle into the neck of the patient is the most risky aspect of the implantation procedure, because subsequent steps of the procedure make use of the implantation path that had already been made by the finder needle. Thus, if damage is done to any structure within the patient's neck by the implantation procedure, it will most likely be done during the initial step of introducing the finder needle. Consequently, the present invention contemplates the use of a robotic device that removes much of the risk associated with manual insertion of the finder needle. Applicants are unaware of any previous attempt to perform percutaneous vagus nerve stimulator implantation with a robotic device. The only prior robotic surgery to implant a vagus nerve stimulator involved the use of the da Vinci surgical system during open neck surgery, under general anesthesia [LOBE T E, Wright S K, Irish M S. Novel uses of surgical robotics in head and neck surgery. J Laparoendosc Adv Surg Tech A.15(June, 2005):647-652].

Figure 9A:
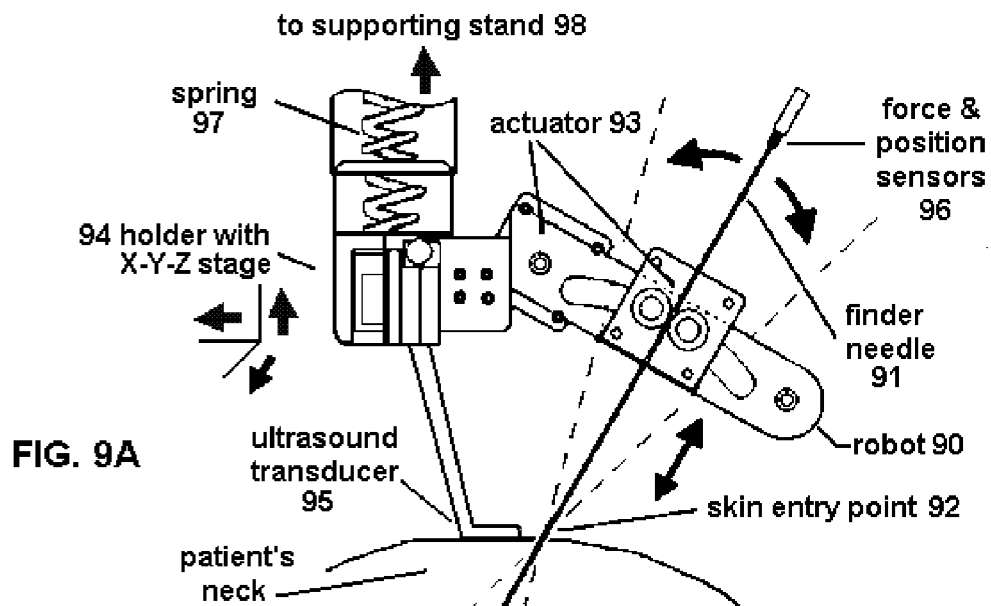
FIG. 9 illustrates a robotic device for the introduction of a finder needle into the neck of a patient (FIG. 9A), the automatic control of which involves processing of ultrasound images and the analysis of data produced by force and position sensors (FIG. 9B).

Components of the implantation robot 90 are shown in FIG. 9A, which inserts a needle 91 into and through an entry point 92 on the patient's skin. Actuators 93 and an X-Y-Z stage 94 that comprise the robot 90 allow the robot to move and insert the needle in many possible directions (shown by arrows in FIG. 9). Feedback control of that movement is possible because the robot also comprises sensors 96 for measuring the force and position experienced by the needle, as well as an ultrasound imaging transducer/probe 95 that measures the progress of the needle 91 in relation to the anatomy of the patient's neck. The transducer is held firmly against the patient's skin by springs 97 within an arm that is used to clamp the robot to a rigid supporting stand 98, wherein the variable angle of the clamping adds additional degrees of freedom to the positioning of the needle.

Figure 9B:
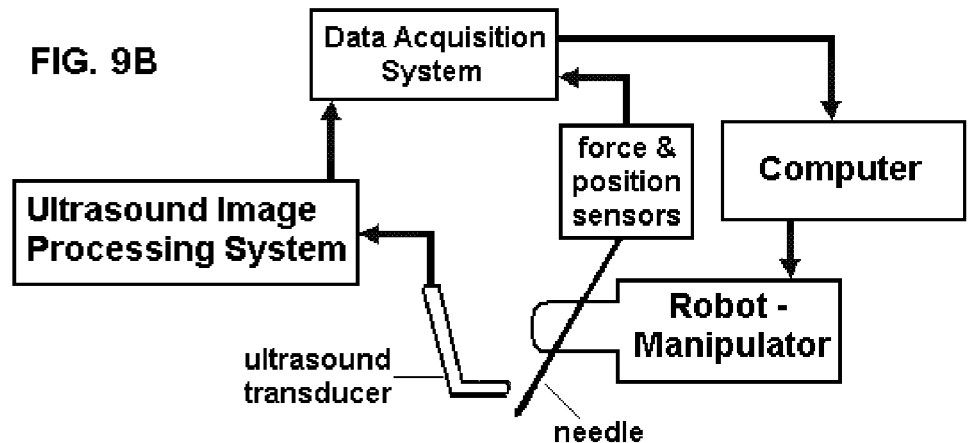

A block diagram showing the robot's control over needle placement is shown in FIG. 9B. Before the needle is advanced to the neck of the patient, the robotic system preferably acquires a digital three-dimensional representation of the anatomy of the patient's neck, which is captured by the ultrasound transducer/probe 95 as the X-Y-Z stage 94 moves the transducer slowly down the patient's neck in a direction perpendicular to the two-dimensional ultrasound image. This image acquisition may be performed in two or more passes, so as to take into account any movement of the patient's neck as a function of the phase of respiration (measured throughout the procedure by inductive plethysmography, mercury in silastic strain gauges, impedance pneumography, etc.). The image acquisition may also be performed with the neck turned to different positions, in order to be able to evaluate the potential movement of a stimulator that is implanted in any potential anatomical configuration or orientation, as the patient turns his or her neck. From the images, the boundaries and identities of tissue within the images may be identified automatically or with manual editing. Using published or otherwise acquired data concerning the generally anisotropic mechanical properties of the various tissues, a tentative three-dimensional mechanical map may be constructed from the image data that can be used to estimate the force and mechanical moment that the finder needle would experience as it progresses through the tissues. Such a map may also be used to predict the probability that the needle would experience one or more deviant movements along the path, brought about, for example, by nonlinearities in the equations of motion for the needle (see references below), uncertainty in the anatomy of the patient, slippage, or potential movement of the neck that is due to the patient's breathing or other factors.

A set of preferred paths that the needle could take within the patient is then calculated, based upon criteria that were described above, and also by the likelihood that a path would also have a low probability of inadvertent needle placement or rotation. The potential paths would include a preferred time-course of needle insertion, such as whether to pause advancement of the needle during a particular phase of respiration, and how fast the needle should be advanced at different locations along the path. A single target path is then selected from among these potential paths.

The needle is then introduced into the patient's neck at the path's entry point 92 and advanced into the neck, while force/moment, position, and ultrasound image data are acquired. Based upon those data, the robot compensates for any discrepancies between the actual needle path and preferred path, until the needle reaches its final destination within the patient's neck. As shown in FIG. 9B, the system automatically processes the ultrasound image data and sends results of the processing, along with needle force and position data to a data acquisition system. Data in that system are then read by a computer, which calculates discrepancies between the actual needle path and the preferred path, and which then controls the actuators of the robot/manipulator to compensate for any path deviations. Significant advantages of the robotic needle insertion include the deliberate creation of paths that are not necessarily straight lines, and the automatic identification or confirmation of tissue layers as the needle is advanced, e.g., automatic recognition of the fact that the carotid sheath has been entered and crossed, by virtue of quantitative changes in the force required to advance the needle there [Niki ABOLHASSANI, Rajni Patel, Mehrdad Moallem. Needle insertion into soft tissue: A survey. Medical Engineering & Physics 29 (2007) 413-431; Kyle B. REED, Ann Majewicz, Vinutha Kallem, Ron Alterovitz, Ken Goldberg, Noah J. Cowan, and Allison M. Okamura. Robot-Assisted Needle Steering. IEEE Robot Autom Mag. 18(April, 2011):35-46; Dedong G O A, Yong Lei, and Haojun Zheng. Needle steering for robot-assisted insertion into soft tissue: a survey. Chinese Journal of Mechanical Engineering 25(April, 2012):629-638; L. BARBE, B. Bayle, M. de Mathelin, A. Gangi. Needle insertions modeling: Identifiability and limitations. Biomedical Signal Processing and Control 2(March, 2007):191-198; Niki ABOLHASSANI, Rajni V. Patel, Farzam Ayazi. Minimization of needle deflection in robot-assisted percutaneous therapy. Int J Med Robotics Comput Assist Surg 3(2007):140-148; J HONG, T Dohi, M Hashizume, K Konishiand N Hata. An ultrasound-driven needle-insertion robot for percutaneous cholecystostomy. Phys. Med. Biol. 49(2004):441-455]. We note that the robot shown in FIG. 9 has a more compact and application-specific design than those used for generic head and neck surgery [OLIVEIRA C M, Nguyen H T, Ferraz A R, Watters K, Rosman B, Rahbar R. Robotic surgery in otolaryngology and head and neck surgery: a review. Minim Invasive Surg. 2012:286563, pp. 1-11]. We note too that the robotic device with ultrasound imaging capability also differs from previous combined ultrasound/stimulation instruments, which use at least one surface electrode to stimulate a nerve and that do not use robotics in the process of inserting an internal electrode to its stimulation site [U.S. Pat. No. 7,789,833, entitled Integrated nerve stimulator and ultrasound imaging device, to URBANO et al].

Figure 10:
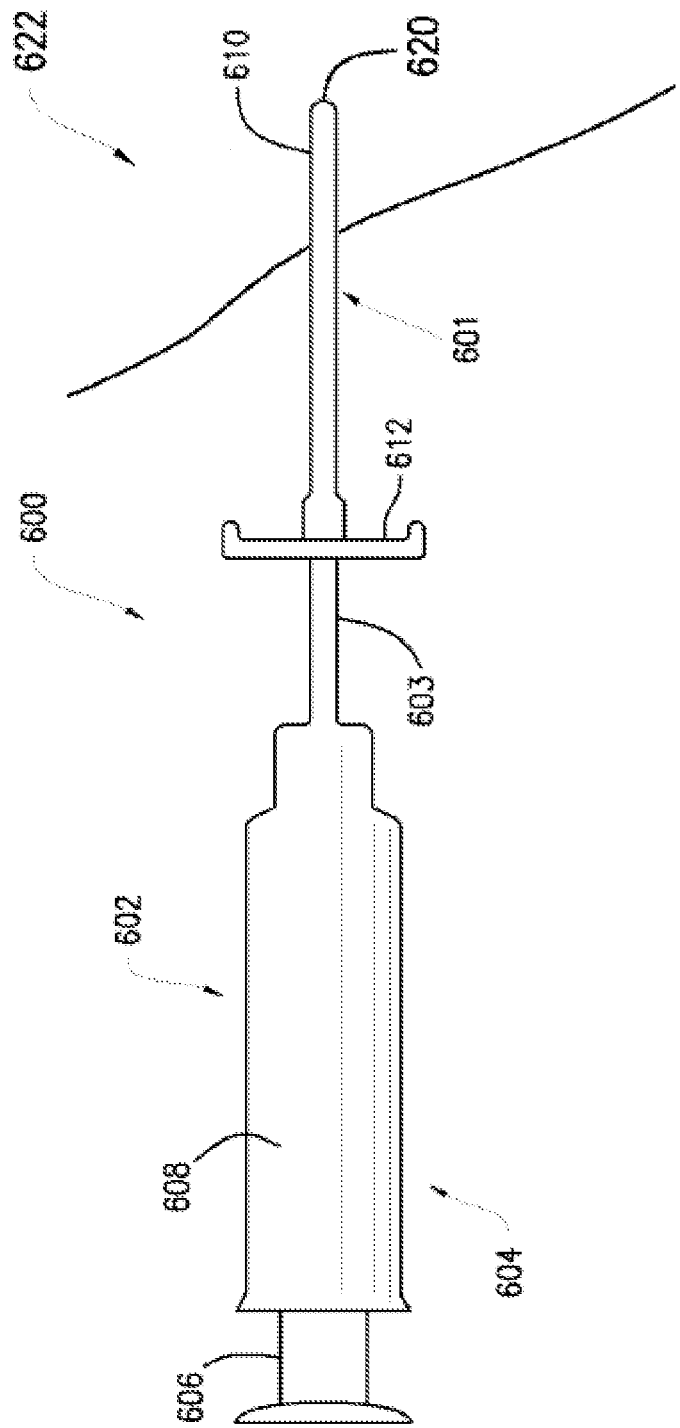
FIG. 10 illustrates an introducer according to one embodiment of the present invention, which is advanced through a percutaneous penetration in a patient to the target region near the carotid sheath.

Once the finder needle is in place, a small incision may be made next to the site at which the finder needle enters the patient's skin, e.g. with a scalpel, to provide access for insertion of a tubular introducer, through which the stimulator device will later be implanted in the patient. The finder needle may be left in place and the introducer may be advanced adjacent to it; or the introducer may be inserted over the finder needle, such that the finder needle initially occupies a lumen within the introducer. In the latter case, the finder needle may be withdrawn once the introducer occupies the path that had been created by the finder needle. FIG. 10 illustrates an exemplary introducer 600 according to one embodiment of the present invention. As shown, introducer 600 includes a needle assembly 602 and a sheath or cannula 601. In this embodiment, needle assembly 602 is a syringe having a flexible hypodermic needle 603 coupled to a piston pump 604 with a plunger 606 that fits within a cylindrical hollow tube 608. If the needle 603 and cannula 601 are inserted over the finder needle, then the piston pump 604 will be attached to the needle 603 after the finder needle is withdrawn, e.g., using a Luer-lock style fitting. As is well known in the art, plunger 606 can be pulled and pushed along the inside of tube 608 to take in and expel liquids or gases through an orifice (not shown) at the open end of tube 608. Cannula 601 includes a base 612 and a hollow tube 610 sized to receive hypodermic needle 603 and stimulator device 300 (as discussed below). Although the specific cannula used is not of criticality to the invention, suitable cannulas can be purchased commercially from Epimed (Epimed International, 13958 Diplomat Drive, Farmers Branch, Tex. 75234). In an alternative non-preferred embodiment, an introducer 600 could be directly inserted into patient without the use of a separate finder needle, or the needle 603 could play the role of the finder needle, with the cannula 601 subsequently inserted over it.

As shown in FIG. 10, tube 610 of introducer 600 is driven through the percutaneous penetration 620 in the neck 622 of a patient and advanced along the same entry path as the finder needle until it reaches the desired depth of placement at the target region, in or around the carotid sheath. The physician may also aspirate needle 603 to ensure that it has not penetrated into a venous or arterial structure. Needle assembly 602 is then removed from cannula 601 by pressing against base 612 while needle assembly 602 is withdrawn.

At this point, a lead blank may be inserted into the cannula 601 and advanced to the target region. A lead blank is an instrument that has the approximate size and shape of the stimulator that will eventually be introduced into the lumen, but that does not contain the stimulator's electrodes. The lead blank is preferably blunt and coated with a material such as Teflon. The purpose of inserting the lead blank into the cannula is to create a sufficiently large and open path, into which the stimulator can eventually be placed. Thus, the present method does not necessarily use traditional dissection prior to implanting of the stimulator. Instead, use of the lead blank is intended to clear out any obstacles in connective tissue that are encountered, for example, in making sure that a hinged stimulator (FIG. 7) has enough room to turn. The alternative would be to actually attempt an endoscopic dissection [U.S. Pat. No. 7,819,883, entitled Method and apparatus for endoscopic access to the vagus nerve, to WESTLUND et al.].

Figure 11:
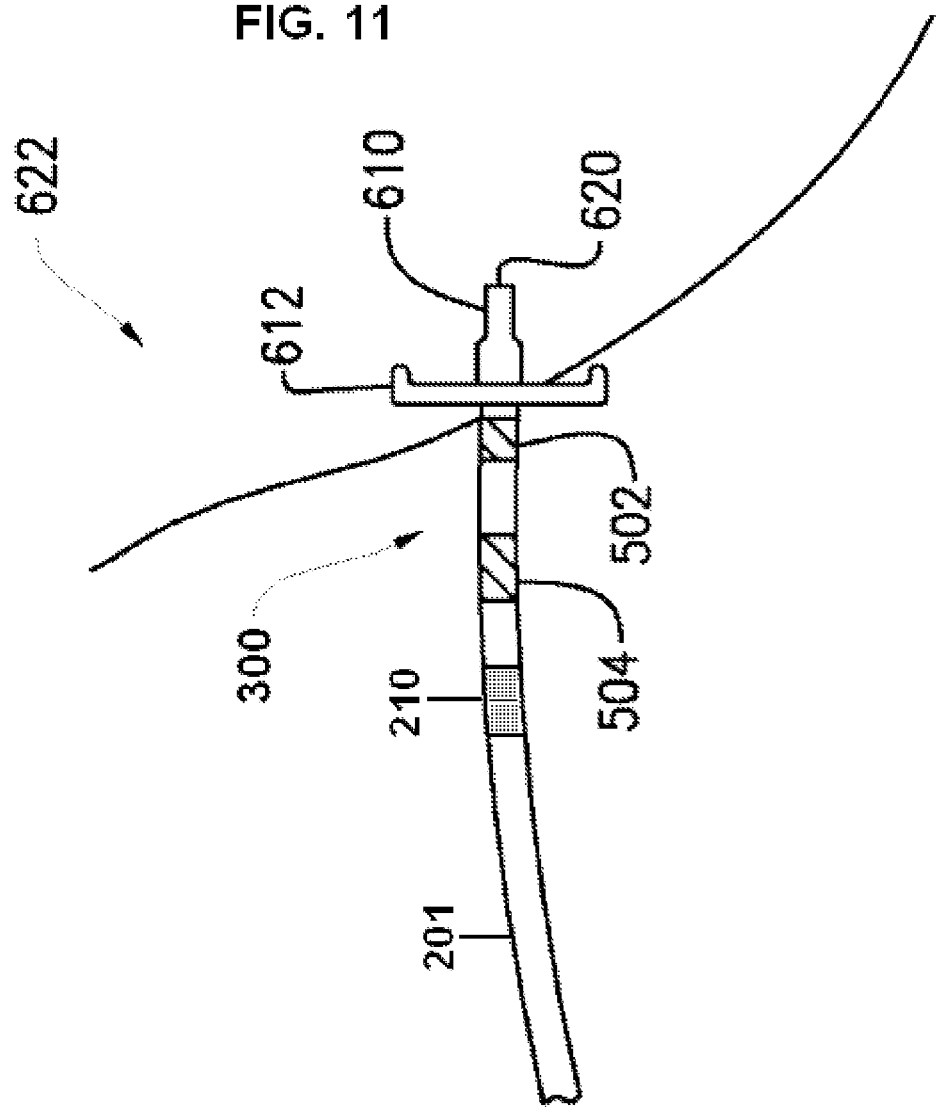
FIG. 11 illustrates an electrode assembly like the one shown in FIG. 2C as it is advanced into and through the introducer to the target region in the patient.

Referring now to FIG. 11, stimulator 300 with tubing 201 that later may be detached at the connecting piece 210 can now be inserted into cannula 601 and advanced to the target region. As shown, the distal end portion of stimulator 300 is sized to fit and easily slide through the inner lumen of cannula 610 such that active and return electrodes 502, 504 can be located at the desired depth/position and orientation in or around the carotid sheath.

Figure 12:
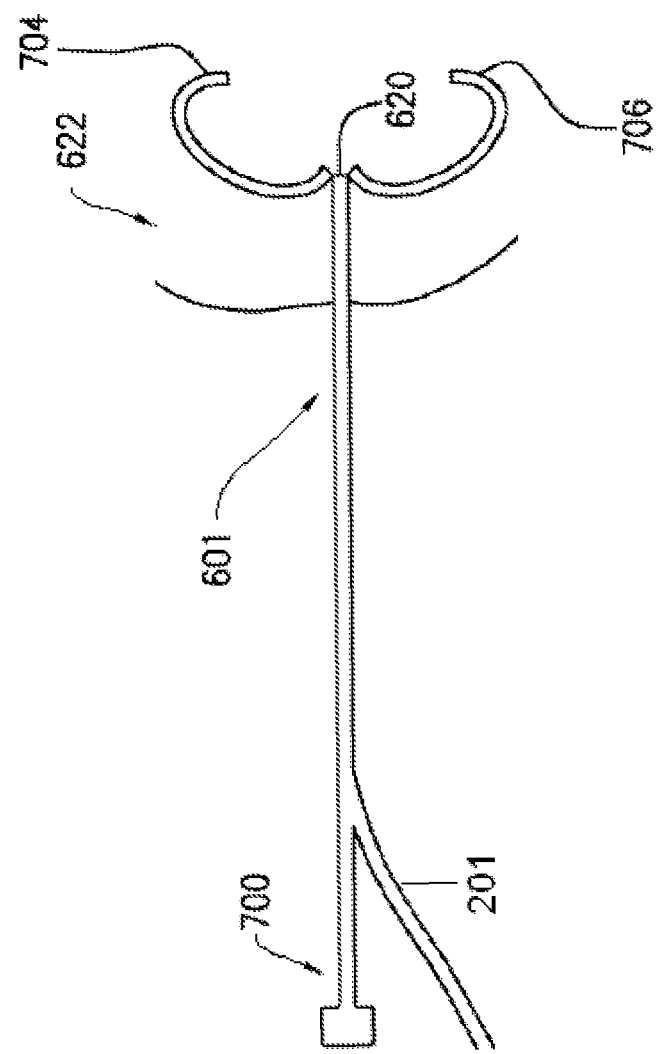
FIG. 12 illustrates the use and removal of a cannula that may be used to facilitate introduction of the stimulator into the neck of the patient.

As shown in FIG. 12, a delivery stylet 700 may be used to provide rigidity to the flexible tubing 201 and shaft of stimulator 300 to assist with the insertion process. A suitable delivery stylet may be purchased commercially from AD-Tech Medical Instrument Corp. (1901 William Street. Racine, Wis.

53401). Of course, it will be recognized by those skilled in the art that stimulator 300 may be advanced to the target region in a variety of manners other than stylet 700. Once in place, the system will be tested to ensure proper functioning, by activating the source of electrical energy and noting the patient's physiological response, as described below.

As also shown in FIG. 12, cannula 601 may now be removed from the patient. In one embodiment, this is accomplished by bending tabs 704, 706 of base 612 downward and pulling them apart, thereby splitting cannula 601 into two pieces. Cannula 601 is then removed while the tubing 201 of stimulator 300 is held securely to prevent migration during cannula 601 removal. Similarly, delivery stylet 700 may be removed from patient leaving only the stimulator 300 in position at the target region. Stimulator 300 is then secured in place within the patient, as described above, for example using surgical glue and/or the deployable springs shown in FIG. 7 or 8. Finally, the tubing 201 of the stimulator 300 is detached from the electrodes and withdrawn, and the point of entry on the patient's skin is bandaged. Alternatively, in a non-preferred embodiment, the tubing 201 is cut to a length ending near skin level, plugged, and sutured just beneath the patient's skin, without being detached from the stimulator.

Monitoring methods may be used during the stimulation implantation procedure to test whether the vagus nerve has been damaged during the procedure. They would also be used after implantation to test operation of the stimulator and to confirm that the implanted stimulator can in fact stimulate the vagus nerve as intended. Such methods have been described for use during thyroid and brainstem surgery to monitor the integrity of a vagus nerve, in which electromyographic monitoring of a laryngeal muscle is used as a safety indicator, and in which the vagus nerve is stimulated, for example, by an electrode placed in an endotracheal tube [SEVERTSON M A, Leonetti J P, Jarocki D. Vagal nerve monitoring: a comparison of techniques in a canine model. Am J Otol 18(March, 1997): 398-400; FRIEDRICH C, Ulmer C, Rieber F, Kern E, Kohler A, Schymik K, Thon K P, Lamadé W. Safety analysis of vagal nerve stimulation for continuous nerve monitoring during thyroid surgery. Laryngoscope 122(September, 2012):1979-1987; DIONIGI G, Chiang F Y, Rausei S, Wu C W, Boni L, Lee K W, Rovera F, Cantone G, Bacuzzi A. Surgical anatomy and neurophysiology of the vagus nerve (VN) for standardised intraoperative neuromonitoring (IONM) of the inferior laryngeal nerve (ILN) during thyroidectomy. Langenbecks Arch Surg 395(July, 2010):893-899; SCHNEIDER R, Przybyl J, Pliquett U, Hermann M, Wehner M, Pietsch U C, König F, Nauss J, Jonas S, Leinung S. A new vagal anchor electrode for real-time monitoring of the recurrent laryngeal nerve. Am J Surg 199(April, 2010):507-514; PHELAN E, Potenza A, Slough C, Zurakowski D, Kamani D, Randolph G. Recurrent laryngeal nerve monitoring during thyroid surgery: normative vagal and recurrent laryngeal nerve electrophysiological data. Otolaryngol Head Neck Surg 147(April, 2012):640-646; SINGH R, Husain A M. Neurophysiologic intraoperative monitoring of the glossopharyngeal and vagus nerves. J Clin Neurophysiol. 2011 December; 28(June, 2011):582-586].

Methods have also been described for monitoring the vagus nerve during open surgery implantation of a vagus nerve stimulator [VAUGHN B V, Bernard E, Lannon S, Mann B, D'Cruz O F, Shockley W, Passanante A. Intraoperative methods for confirmation of correct placement of the vagus nerve stimulator. Epileptic Disord 3(February, 2001):75-78]. In a commonly assigned, co-pending application, entitled Devices and methods for monitoring non-invasive vagus nerve stimulation, which is hereby incorporated by reference, Applicant disclosed improved methods for verifying the operation of a vagus nerve stimulation device. Those disclosed methods may also be used during the implantation procedure to verify that the vagus nerve remains undamaged. As an example, the patient may be requested to vocalize a vowel such as /a/ over several voice ranges (continuous glissando), before, during, and after the implantation procedure. An acoustic analysis of the sounds may be used to infer whether the vagus nerve is damaged and whether electrical stimulation of the vagus nerve by electrodes of the implanted stimulator is in fact having an effect. This is because such electrical stimulation may bring about subtle voice changes through its sensitive effect on a branch of the vagus nerve, the recurrent laryngeal nerve.

Although this disclosure relates specifically to the electrical stimulation of a vagus nerve, it will be appreciated that the systems and methods of the present invention can be adapted for use with other tissues and nerves of the body, including but not limited to other parasympathetic nerves, sympathetic nerves, spinal or cranial nerves, e.g., optic nerve, facial nerves, vestibulocochlear nerves and the like. In addition, embodiments of the present invention can be applied to treat symptoms of ailments or the ailments themselves, when used in conjunction with other procedures, including open procedures, intravascular procedures, interventional cardiology procedures, urology, laparoscopy, general surgery, arthroscopy, thoracoscopy or other cardiac procedures, cosmetic surgery, orthopedics, gynecology, otorhinolaryngology, spinal and neurologic procedures, oncology procedures and the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a condition or a symptom of a patient, the method comprising:
   receiving an input signal wirelessly from a controller at a stimulation device positioned at a target site adjacent to or near a nerve within a neck of the patient, wherein the input signal contains electrical energy, wherein the stimulation device comprises an antenna, a storage device coupled to the antenna, and an electrode, wherein the antenna receives the input signal, wherein the storage device stores the electrical energy;
   generating an electrical impulse within the stimulation device with the electrical energy from the storage device, wherein the electrical impulse comprises a fixed amplitude;
   varying a duration of the electrical impulse via the stimulation device; and
   applying the electrical impulse to the nerve via the electrode, wherein the electrical impulse is sufficient to modulate the nerve and treat the condition or the symptom.

2. The method of claim 1, wherein the controller is located remotely from the stimulation device and the receiving is through electrical radiative coupling.

3. The method of claim 2, wherein the controller is located external to the patient.

4. The method of claim 1, wherein the electrical impulse comprises one or more pulses, wherein each of the one or more pulses comprises a fixed amplitude and a fixed duration, and wherein the electrical impulse comprises a duration equal to a combined duration of the fixed duration of each of the one or more pulses.

5. The method of claim 4, wherein the varying is by varying a number of the one or more pulses within the electrical impulse.

6. The method of claim 1, further comprising:
storing the electrical energy from the input signal within the stimulation device via the storage device; and
releasing the electrical energy from the storage device to a pulse generator within the stimulation device to generate the electrical impulse, wherein the pulse generator is coupled to the electrode.

7. The method of claim 6, wherein the electrical energy is stored within a capacitor in the stimulation device, wherein the storage device comprises the capacitor.

8. The method of claim 7, wherein the electrical energy is stored during a period of time between a generation of electrical impulses.

9. The method of claim 1, wherein the electrical impulse comprises a fixed voltage.

10. The method of claim 1, wherein the electrical impulse comprises a fixed current.

11. The method of claim 4, wherein the fixed amplitude of each of the one or more pulses is from about 1 V to about 20 V.

12. The method of claim 4, wherein the fixed amplitude of each of the one or more pulses is about 10 V.

13. The method of claim 4, wherein the fixed duration of each of the one or more pulses is from about 100 uS to about 400 uS.

14. The method of claim 4, wherein the fixed duration of each of the one or more pulses is about 200 uS.

15. The method of claim 4, wherein the duration of the electrical impulse is from about 200 uS to about 1000 uS.

16. The method of claim 4 wherein the duration of the electrical impulse occurs during a stimulation and rising phase of the nerve.

17. The method of claim 2, wherein the input signal is received via a carrier signal comprising a frequency from about 300 MHz to about 6 GHz.

18. The method of claim 17, wherein the carrier signal comprises a frequency from about 800 MHz to about 1.2 GHz.

19. The method of claim 1, wherein the electrical impulse comprises a frequency from about 1 Hz to about 50 Hz.

20. The method of claim 1 wherein the electrical impulse generates an electric field at a vagus nerve above a threshold for generating action potentials within A and B fibers of the vagus nerve and below a threshold for generating action potentials within C fibers of the vagus nerve.

21. A stimulation device for treating a condition of a patient, the stimulation device comprising:
an enclosure configured for positioning adjacent to or near a nerve within a neck of the patient;
an antenna configured to receive an input signal from a power source located remotely from the enclosure, wherein the input signal comprises electrical energy, wherein the enclosure comprises the antenna;
a storage device coupled to the antenna, wherein the storage device is configured to store the electrical energy, wherein the enclosure comprises the storage device;
a pulse generator coupled to the storage device, wherein the pulse generator is configured to generate an electrical impulse based on the electrical energy stored in the storage device, wherein the electrical impulse comprises a fixed amplitude and a variable duration, wherein the enclosure comprises the pulse generator, wherein the electrical impulse comprises one or more pulses, wherein each of the one or more pulses comprises a fixed amplitude and a fixed duration, wherein the electrical impulse comprises a duration equal to a combined duration of the fixed duration of each of the one or more pulses, wherein the fixed amplitude of each of the one or more pulses is from about 1 V to about 20 V; and
one or more electrodes housed within the enclosure and coupled to the pulse generator, wherein the one or more electrodes is configured to conduct the electrical impulse to the nerve sufficient to modulate the nerve.

22. The stimulation device of claim 21, wherein the antenna is housed within the enclosure.

23. The stimulation device of claim 21, wherein the pulse generator is configured to vary a number of the one or more pulses within the electrical impulse to vary the duration of the electrical impulse.

24. The stimulation device of claim 21, wherein the storage device is a capacitor configured to store the electrical energy during a period of time between a generation of electrical impulses via the pulse generator.

25. The stimulation device of claim 21, wherein the fixed amplitude of each of the one or more pulses is about 10 V.

26. The stimulation device of claim 21, wherein the input signal is received from the power source through electrical radiative coupling on a carrier signal comprising a frequency from about 300 MHz to about 6 GHz.

27. The stimulation device of claim 21, wherein the electrical impulse comprises a frequency from about 1 Hz to about 50 Hz.

28. A stimulation device for treating a condition of a patient, the stimulation device comprising:
an enclosure configured for positioning adjacent to or near a nerve within a neck of the patient;
an antenna configured to receive an input signal from a power source located remotely from the enclosure, wherein the input signal comprises electrical energy, wherein the enclosure comprises the antenna;
a storage device coupled to the antenna, wherein the storage device is configured to store the electrical energy, wherein the enclosure comprises the storage device;
a pulse generator coupled to the storage device, wherein the pulse generator is configured to generate an electrical impulse based on the electrical energy stored in the storage device, wherein the electrical impulse comprises a fixed amplitude and a variable duration, wherein the enclosure comprises the pulse generator; and
one or more electrodes housed within the enclosure and coupled to the pulse generator, wherein the one or more electrodes is configured to conduct the electrical impulse to the nerve sufficient to modulate the nerve, wherein the electrical impulse comprises a fixed voltage.

29. A stimulation device for treating a condition of a patient, the stimulation device comprising:
an enclosure configured for positioning adjacent to or near a nerve within a neck of the patient;
an antenna configured to receive an input signal from a power source located remotely from the enclosure, wherein the input signal comprises electrical energy, wherein the enclosure comprises the antenna;
a storage device coupled to the antenna, wherein the storage device is configured to store the electrical energy, wherein the enclosure comprises the storage device;
a pulse generator coupled to the storage device, wherein the pulse generator is configured to generate an electrical impulse based on the electrical energy stored in the storage device, wherein the electrical impulse comprises a fixed amplitude and a variable duration, wherein the enclosure comprises the pulse generator; and one or more electrodes housed within the enclosure and coupled to the pulse generator, wherein the one or more electrodes is configured to conduct the electrical impulse to the nerve sufficient to modulate the nerve, wherein the electrical impulse comprises a fixed current.

30. The stimulation device of claim 28, wherein the fixed amplitude of each of the one or more pulses is from about 1 V to about 20 V.

31. A stimulation device for treating a condition of a patient, the stimulation device comprising:

an enclosure configured for positioning adjacent to or near a nerve within a neck of the patient;

an antenna configured to receive an input signal from a power source located remotely from the enclosure, wherein the input signal comprises electrical energy, wherein the enclosure comprises the antenna;

a storage device coupled to the antenna, wherein the storage device is configured to store the electrical energy, wherein the enclosure comprises the storage device;

a pulse generator coupled to the storage device, wherein the pulse generator is configured to generate an electrical impulse based on the electrical energy stored in the storage device, wherein the electrical impulse comprises a fixed amplitude and a variable duration, wherein the enclosure comprises the pulse generator; and one or more electrodes housed within the enclosure and coupled to the pulse generator, wherein the one or more electrodes is configured to conduct the electrical impulse to the nerve sufficient to modulate the nerve, wherein the electrical impulse comprises one or more pulses, wherein each of the one or more pulses comprises a fixed amplitude and a fixed duration, wherein the electrical impulse comprises a duration equal to a combined duration of the fixed duration of each of the one or more pulses, wherein the fixed duration of each of the one or more pulses is from about 100 uS to about 400 uS.

32. The stimulation device of claim 31, wherein the fixed duration of each of the one or more pulses is about 200 uS.

33. A stimulation device for treating a condition of a patient, the stimulation device comprising:

an enclosure configured for positioning adjacent to or near a nerve within a neck of the patient;

an antenna configured to receive an input signal from a power source located remotely from the enclosure, wherein the input signal comprises electrical energy, wherein the enclosure comprises the antenna;

a storage device coupled to the antenna, wherein the storage device is configured to store the electrical energy, wherein the enclosure comprises the storage device;

a pulse generator coupled to the storage device, wherein the pulse generator is configured to generate an electrical impulse based on the electrical energy stored in the storage device, wherein the electrical impulse comprises a fixed amplitude and a variable duration, wherein the enclosure comprises the pulse generator; and one or more electrodes housed within the enclosure and coupled to the pulse generator, wherein the one or more electrodes is configured to conduct the electrical impulse to the nerve sufficient to modulate the nerve, wherein the electrical impulse comprises one or more pulses, wherein each of the one or more pulses comprises a fixed amplitude and a fixed duration, wherein the electrical impulse comprises a duration equal to a combined duration of the fixed duration of each of the one or more pulses, wherein the duration of the electrical impulse is from about 200 uS to about 1000 uS.

34. A stimulation device for treating a condition of a patient, the stimulation device comprising:

an enclosure configured for positioning adjacent to or near a nerve within a neck of the patient;

an antenna configured to receive an input signal from a power source located remotely from the enclosure, wherein the input signal comprises electrical energy, wherein the enclosure comprises the antenna;

a storage device coupled to the antenna, wherein the storage device is configured to store the electrical energy, wherein the enclosure comprises the storage device;

a pulse generator coupled to the storage device, wherein the pulse generator is configured to generate an electrical impulse based on the electrical energy stored in the storage device, wherein the electrical impulse comprises a fixed amplitude and a variable duration, wherein the enclosure comprises the pulse generator; and one or more electrodes housed within the enclosure and coupled to the pulse generator, wherein the one or more electrodes is configured to conduct the electrical impulse to the nerve sufficient to modulate the nerve, wherein the electrical impulse comprises one or more pulses, wherein each of the one or more pulses comprises a fixed amplitude and a fixed duration, wherein the electrical impulse comprises a duration equal to a combined duration of the fixed duration of each of the one or more pulses, wherein the duration of the electrical impulse occurs during a stimulation and rising phase of the nerve.

35. A method for facilitating a treatment of at least one of a condition or a symptom of a patient, the method comprising:

sending an input signal wirelessly from a controller to a stimulation device positioned at a target site adjacent to or near a nerve within a neck of the patient, wherein the input signal contains electrical energy, wherein the stimulation device comprises an antenna, a storage device coupled to the antenna, and an electrode, wherein the antenna is configured to receive the input signal, wherein the storage device is configured to store the electrical energy, wherein the stimulation device is configured to generate an electrical impulse within the stimulation device with the electrical energy from the storage device, wherein the electrical impulse is configured to comprise a fixed amplitude, wherein the stimulation device is configured to vary a duration of the electrical impulse, wherein the electrode is configured to apply the electrical impulse to the nerve, wherein the electrical impulse is configured to be sufficient to modulate the nerve and treat at least one of the condition or the symptom.

* * * * *